US012636281B2

(12) United States Patent
Park et al.

(10) Patent No.: US 12,636,281 B2
(45) Date of Patent: May 26, 2026

(54) DIETARY SUPPLEMENTS TO AMELIORATE DIETARY INADEQUACIES RELATED TO BRAIN HEALTH OR NEURODEGENERATIVE DISEASES, AND METHODS TO DESIGN DIETARY SUPPLEMENTS

(71) Applicant: NEURORESERVE INC., Las Vegas, NV (US)

(72) Inventors: Edward S. Park, Las Vegas, NV (US); Matthew M. Crane, Seattle, WA (US); John F. O'Connell, Collegeville, PA (US); John C. Wallingford, Spokane, WA (US); Elaine M. Mann, Chelsea, MA (US)

( * ) Notice: Subject to any disclaimer, the term of this patent is extended or adjusted under 35 U.S.C. 154(b) by 935 days.

(21) Appl. No.: 17/633,699

(22) PCT Filed: Aug. 19, 2020

(86) PCT No.: PCT/US2020/047013

§ 371 (c)(1),
(2) Date: Feb. 8, 2022

(87) PCT Pub. No.: WO2021/034942

PCT Pub. Date: Feb. 25, 2021

(65) Prior Publication Data

US 2022/0313673 A1 Oct. 6, 2022

Related U.S. Application Data

(60) Provisional application No. 62/888,721, filed on Aug. 19, 2019.

(51) Int. Cl.

| | |
|---|---|
| *A61K 31/455* | (2006.01) |
| *A23L 33/12* | (2016.01) |
| *A23L 33/155* | (2016.01) |
| *A23L 33/165* | (2016.01) |
| *A61K 31/05* | (2006.01) |
| *A61K 31/09* | (2006.01) |
| *A61K 31/198* | (2006.01) |
| *A61K 31/352* | (2006.01) |
| *A61K 31/353* | (2006.01) |
| *A61K 31/355* | (2006.01) |
| *A61K 31/593* | (2006.01) |
| *A61K 31/685* | (2006.01) |
| *A61K 31/714* | (2006.01) |
| *A61K 33/06* | (2006.01) |
| *A61P 3/02* | (2006.01) |
| *A61P 25/28* | (2006.01) |

(52) U.S. Cl.
CPC ............ *A61K 31/455* (2013.01); *A23L 33/12* (2016.08); *A23L 33/155* (2016.08); *A23L 33/165* (2016.08); *A61K 31/05* (2013.01); *A61K 31/09* (2013.01); *A61K 31/198*

(2013.01); *A61K 31/352* (2013.01); *A61K 31/353* (2013.01); *A61K 31/355* (2013.01); *A61K 31/593* (2013.01); *A61K 31/685* (2013.01); *A61K 31/714* (2013.01); *A61K 33/06* (2013.01); *A61P 3/02* (2018.01); *A61P 25/28* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 2010/0104696 A1* | 4/2010 | Banavara | ................ A23L 33/40 426/72 |
| 2015/0037455 A1* | 2/2015 | Chichlowski | ........ A61K 31/202 426/71 |
| 2016/0310529 A1 | 10/2016 | Schneider et al. | |

OTHER PUBLICATIONS

Alcalay et al. "The Association between Mediterranean Diet Adherence and Parkinson's Disease," Mov. Disord. 27, 771-774. (2012).
Aridi et al., S. Y., "The Association between the Mediterranean Dietary Pattern and Cognitive Health: A Systematic Review," Nutrients 2017, 9, 674, pp. 1-23.
Gao et al., "Prospective study of dietary pattern and risk of Parkinson disease," Am. J. Clin. Nutr. 2007;86: pp. 1486-1494.
Gu et al., "Food Combination and Alzheimer Disease Risk: A Protective Diet," JAMA Arch Neurol. (Jun. 2010) vol. 67, No. 6, pp. 699-706.
Hardman et al., "Adherence to a Mediterranean-Style Diet and Effects on Cognition in Adults: A Qualitative Evaluation and Systematic Review of Longitudinal and Prospective Trials," Frontiers in Nutrition vol. 3, Article 22, pp. 1-13. (2016).
International Search Report and Written Opinion for International PCT Application No. PCT/US2020/047013 dated Jan. 6, 2021.
Kesse-Guyot et al., "A Healthy Dietary Pattern at Midlife is Associated with Subsequent Cognitive Performance," J. Nutr. 142, pp. 909-915. (2012).
Knight et al., "Is the Mediterranean diet a feasible approach to preserving cognitive function and reducing risk of dementia for older adults in Western countries? New insights and future directions," Ageing Res. Rev. 25, pp. 85-101 (2016).
Loughrey et al., "The Impact of the Mediterranean Diet on the Cognitive Functioning of Healthy Older Adults: A Systematic Review and Meta-Analysis," Adv. Nutr. 2017; 8, pp. 571-586.
Morris et al., "MIND diet associated with reduced incidence of Alzheimer's disease," Alzheimer's Dement. 11, pp. 1007-1014. (2015).

(Continued)

*Primary Examiner* — Danah Al-Awadi

(74) *Attorney, Agent, or Firm* — Sam Pierce

(57) ABSTRACT

The dietary supplements of various embodiments comprise a water-soluble vitamin component, an oil-soluble vitamin component, magnesium or derivatives thereof, a primary polyphenolic compound, a secondary polyphenolic compound, and an omega-3-phospholipid complex. The methods include maintaining health, maintaining brain health and reducing the risk or rate of neurodegeneration or cognitive decline. Methods, including algorithms, for systematically determining a dietary supplement are also described.

18 Claims, 2 Drawing Sheets

(56)    References Cited

OTHER PUBLICATIONS

Morris et al., "MIND diet slows cognitive decline with aging," Alzheimer's Dement. 11, pp. 1015-1022. (2015).
Tangney et al. "Relation of DASH- and Mediterranean-like dietary patterns to cognitive decline in older persons," Neurology 83, pp. 1410-1416. (2014).

* cited by examiner

FIG. 2

DIETARY SUPPLEMENTS TO AMELIORATE DIETARY INADEQUACIES RELATED TO BRAIN HEALTH OR NEURODEGENERATIVE DISEASES, AND METHODS TO DESIGN DIETARY SUPPLEMENTS

CROSS-REFERENCE TO RELATED APPLICATIONS

This application claims the benefit of U.S. Provisional Application No. 62/888,721 filed Aug. 19, 2019, of which is incorporated herein by reference in its entirety.

SUMMARY OF THE INVENTION

This invention relates to dietary supplement compositions that protect and support brain health or reduce the risk of neurodegenerative diseases, comprising six component groupings: a water-soluble vitamin component, an oil-soluble vitamin component, magnesium or derivatives thereof, a primary polyphenolic compound, a secondary polyphenolic compound, and an omega-3-phospholipid complex. The compositions are built upon the framework of emerging findings of the neuroprotective effects of specific dietary patterns. Also, this invention relates to methods to protect and support brain health or reduce the risk of neurodegenerative diseases by administering the compositions described herein to a subject, such as a human or other mammal. Additionally, the invention relates to methods to design dietary supplements, using a multi-step algorithm to process evidentiary information across multiple dimensions, including available epidemiological, deficiency, clinical, mechanism of action, and safety data, which supports the inclusion or exclusion of certain nutrients in product formulations.

Embodiments disclosed herein are directed to dietary supplements comprising a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of docosahexaenoic acid (DHA), eicosapentaenoic acid (EPA), and combinations thereof.

Embodiments disclosed herein are directed to the following methods: maintaining or improving brain health, reducing the risk of neurodegenerative disease (such as Alzheimer's or Parkinson's disease), slowing or protecting against the development of neurodegenerative disease or such disease pathology, ameliorating certain micronutrient consumption (intake) inadequacies associated with maintenance of brain health, cognitive decline, risk of neurodegenerative disease, or neurodegenerative pathology, reducing the risk or rate of cognitive decline, providing intakes of certain nutrients so as to mimic neuroprotective dietary patterns, maintaining or improving a mental or cognitive quality, maintaining or improving cerebrovascular health, maintaining or improving brain trophic factors, maintaining or improving gut health, protecting from or treating toxin or toxic exposures, treating neurodegenerative disease, improving or maintaining health, and maintaining or improving certain areas of health (such as immune, eye, cardiovascular, metabolic, and longevity), in a subject comprising administering to the subject a dietary supplement comprising a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments described herein are directed to methods, including algorithms, for determining a dietary supplement comprising: (i) selection of dietary patterns, including those whose adherence is related to brain health, neurodegenerative disease incidence, neurodegenerative disease pathogenesis, pathology or progression, and/or cognitive decline that is typically associated with aging, (ii) selection and/or definition of dietary components from such dietary patterns, (iii) transformation of dietary components into constituent nutrients, (iv) primary screening of constituent nutrients against human epidemiological evidence that relates such nutrients to outcomes in brain health, neurodegenerative disease incidence, neurodegenerative disease pathogenesis, pathology or progression, and/or cognitive decline that is typically associated with aging, (v) identifying nutrients for which there exist dietary inadequacies based on reference intakes, guidelines and/or changes in age-related requirements, (vi) confirmation of mechanism(s) of action (MOAs) by nutrients of interest that are relevant to the biological hallmarks of neurodegenerative diseases or aging of the brain, (vii) evaluation of the expected benefits and safety of nutrients of interest. Such method would yield a score, weighting or rating for each nutrient of interest to support its inclusion or exclusion in formulations and recommended combination of such nutrients.

DESCRIPTION OF THE DRAWINGS

For a fuller understanding of the nature and advantages of the present embodiments, reference should be had to the following detailed description taken in connection with the accompanying drawings, in which:

FIG. 2 represents an output matrix from the algorithm to design dietary supplements as described herein for a select group of nutrients (visual ratings via color intensity) across five dimensions of evaluation.

DETAILED DESCRIPTION

Figure 1:
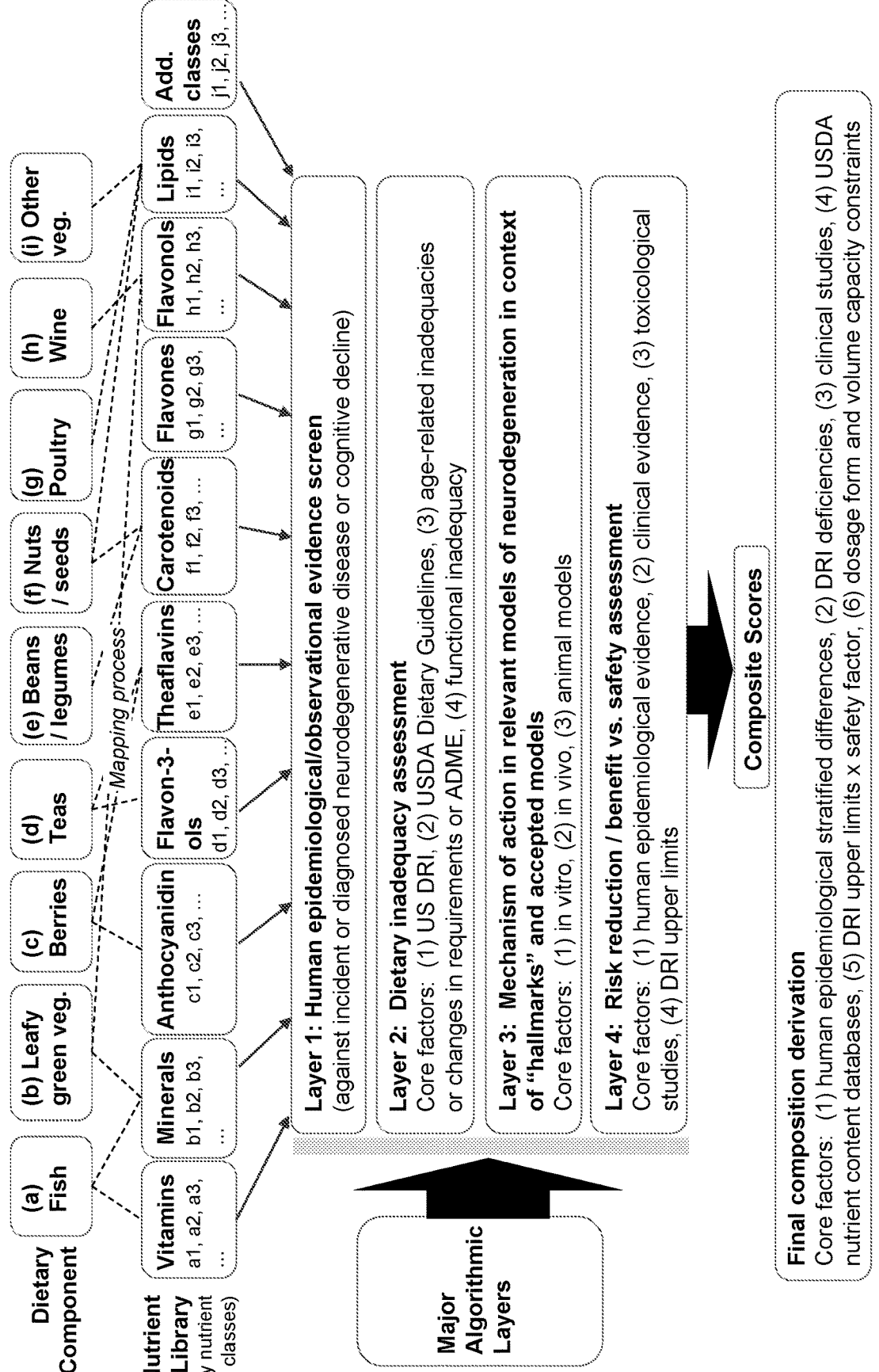
FIG. 1 depicts, as a flow diagram, the method and algorithm utilized to develop a dietary supplement as described herein.

The maintenance of brain health is a rapidly growing need and concern, and the prospect of age-related cognitive decline and neurodegeneration and its associated diseases is both terrifying and unique to society at-large. Examples of neurodegenerative diseases are Alzheimer's disease (AD), Parkinson's disease (PD), amyotrophic lateral sclerosis (ALS), Huntington's disease, and the effects of traumatic brain injuries (TBI). The common driver for neurodegenerative diseases is the progressive loss of the structure and function, and eventual death, of neurons and portions of the brain in-aggregate—and the common outcome is the destruction of our memories, cognitive ability, mobility or combinations thereof.

What makes neurodegenerative diseases so unique is that they are "more than fatal." As the brain disintegrates, these diseases destroy the foundation of who persons are through dementia, physical debilitation, social isolation, psychological decline, and/or institutionalization. Additionally, the process from diagnosis to death is tortuously slow, prolonging the suffering that patients, family, and friends must endure. Also, unlike other disease areas, such as cancer, cardiovascular disease, and diabetes, there are no effective disease-modifying treatments available for people stricken with neurodegenerative disease.

Thus, neurodegeneration and neurodegenerative diseases present a severe and rapidly growing public health threat, especially as the average individual lives longer, which will put tremendous and unsustainable pressure our families, health care systems, governments, and other institutions without new approaches to contain the current trajectory.

Neurodegeneration is extremely complex and multi-factorial; which in turn makes it extremely difficult to study, as opposed to heart disease or even cancer. The changes in brain chemistry and structure begin decades before symptoms are noticed. Researchers are faced with a multitude of hurdles to studying neurodegeneration; for example, there are no reliable or easily-accessible biomarkers for early detection and/or assessment of disease modification, and animal models translate poorly to humans. As a result, prior candidate therapies or drugs have largely met with failure in the treatment or post-diagnosis phase. The past 15 years were particularly frustrating for Alzheimer's disease, marked by the failure of hundreds of clinical studies for drug candidates. Similarly for Parkinson's disease, there have been no novel disease-modifying drugs approved in the U.S. over the past few decades, only drugs with improvements in symptom-level treatment. It is clear that the conventional model of drug development (a single molecule targeting a single biochemical mechanism) is unlikely to be a viable solution to address the complexity of neurodegenerative disease, especially in later stages after people are clinically diagnosed.

Rather than focusing on a cure after diagnosis, a shift toward maintaining brain health, risk reduction, or prevention is critical. Recently, the scientific and medical communities have acknowledged the importance of maintaining brain health, intervening in cognitive decline, and intervening in neurodegenerative processes decades before potential diagnosis or symptoms, and they are now advocating for and exploring prevention as a strategy; lifestyle interventions and nutritional interventions are key factors. Accordingly, there exists a need for rationally designed nutritional products (for example, dietary supplements) and rational design methods to develop dietary supplements for long-term brain health, i.e. dietary supplements to maintain, protect, and support brain health and/or prevent, reduce the risk of, delay, stabilize or reverse neurodegenerative diseases, pathologies, or cognitive decline.

A potential tool to investigate the effect of dietary supplementation as a risk reduction or preventive approach against neurodegeneration is the primary prevention study. The challenge is that primary prevention studies are difficult to conduct and largely impractical given the state-of-the-art; thus, there have been very few such studies, which slows the pace of innovation in this field. For example, one major U.S. primary prevention study conducted for neurodegeneration investigated supplementation of a *Ginkgo biloba* extract (*Ginkgo* Evaluation of Memory study (GEM)). Primary prevention studies like GEM require extensive size and scope that limit feasibility, such as large study populations and long follow-up periods (many years), given the generally low incidence of neurodegenerative disease in a study population that starts healthy or asymptomatic. To limit the required follow-up period, primary prevention studies typically recruit older or elderly subjects (for example, >75 years old for GEM); however, the study intervention may have limited or no effect on subjects of advanced age because the intervention is introduced too late in life, well after a critical period of exposure to risk factors and after irreversible or unmodifiable pre-symptomatic disease progression has taken place. In addition, there is greater risk of co-morbidities or competing risks of death in older or elderly subjects, which increases the rate of attrition and is a major source of potential bias in such studies. Moreover, the burden of study visits (for example, the duration, frequency, and/or invasiveness of cognitive tests or imaging) and perceived lack of efficacy can further cause attrition and subsequent loss of data. Standardization is particularly difficult, given that such methods should be applicable and valid across cultures and languages. Other problems include the selection of the study population and absence of reliable and inexpensive biomarkers of brain health or neurodegenerative disease progression, particularly in the early or pre-symptomatic phases, and ethical restrictions regarding the conduct of studies in which there are known nutrient deficiencies in their human subjects.

Especially for risk reduction and prevention, these studies typically rely only on a single factor or agent, which neglects the potential for multiple, interlinked nutritional interventions or factors that could prove efficacious when implemented concurrently. Some initial studies that implement more than one intervention have been conducted or are currently being developed. However, they face similar challenges as mentioned above, as they require intensive interventions and study visits that substantially increase cost and burden.

As a result, rational (systematic) and comprehensive (multi-nutrient/multi-factor) design is absent from products in the marketplace for dietary supplements aimed at brain health and nutrition. Thus, such formulations predominantly are ill-equipped to address the maintenance of brain health and the corresponding time scales and pathologies involved in aging.

Recently, prospective observational studies, particularly in the past 10 years, have increased in sophistication, scope, and precision, and they open a new option for rational design and the basis of new inventions of dietary supplements for brain health maintenance and/or neurodegeneration. These studies longitudinally track the outcomes of large, prospective cohorts of study subjects, collect information spanning multiple risk factors and/or domains of behavior (for example, genetics, co-morbidities, dietary patterns, physical activity, mentally stimulating activities), and may stratify data or control for potentially confounding variables through sophisticated statistical methods. In one example, a large-scale observational study was used to develop a dietary pattern, referred to as the MIND diet (Mediterranean-DASH Intervention for Neurodegenerative Delay), that is strongly suggested to reduce the risk of incident neurodegenerative disease (in this case, Alzheimer's disease) and slow cognitive decline. This was achieved by relating the results from an extensive food frequency questionnaire (measuring intake of >130 food items), specifically validated to assess dietary patterns regardless of advanced age, chronic health conditions, and even cognitive impairment, to the precise dietary components of the MIND diet.

In addition to the MIND diet, the evidence that links other dietary patterns to long-term risk of Alzheimer's disease, Parkinson's disease, dementia, cognitive decline or other aspects of brain health has grown substantially in recent years. Many of such studies employed the human prospective observational methods described above, following study subjects from a few years to over 10 years to monitor brain outcomes. The predominant dietary pattern to demonstrate neuroprotective effects is the Mediterranean diet (MeDi). Also, the DASH (Dietary Approaches to Stop Hypertension) dietary pattern has been shown to be neuroprotective. Furthermore, there are neuroprotective dietary patterns that have been derived by statistical modeling of dietary data collected from sample populations. Such dietary patterns are a posteriori patterns, as opposed to a priori patterns that are based directly on culture (like the MeDi) or based on specific recommendations (like the DASH or MIND). Examples of a posteriori dietary patterns are the "Healthy," "Prudent" or "Protective" patterns. In totality, when looking at the MeDi, DASH, MIND, and a posteriori dietary patterns linked to brain health, there are striking commonalities across them regarding beneficial factors they aim to promote and detrimental factors they aim to avoid. Such dietary patterns can provide a governing framework upon which to design novel dietary supplement compositions, which represent coherent, synergistic groupings of brain-relevant nutrients by virtue of their co-location together in such dietary patterns. Presented herein are novel dietary supplement compositions designed within such a framework.

Also, presented herein is a unique algorithmic process used to rationally design dietary supplements for maintaining health, preventing or slowing neurodegeneration, or preventing other age-related diseases. This process begins with dietary patterns and dietary components as defined in large-scale observational nutritional studies. It relies upon epidemiological/observational cohort data in the primary screen for nutrients. And includes multiple analyses in stages (or layers): epidemiology, dietary inadequacies, use of age-related changes in nutrient needs (i.e. the absorption, distribution, metabolism, and excretion (ADME) of said nutrient), functional inadequacies, mechanisms of action, benefit assessments, and safety profiles.

Resulting dosage levels typically mimic adequate or repletion/high-intake within the bounds of realistic dietary consumption (diet-achievable intake), which is different than the super- or mega-dose route that typical dietary supplements utilize. Determination of the dosages of each component utilize United States Department of Agriculture (USDA) nutrient content databases, reference intakes, composite diets or combinations thereof.

Various aspects will be described in detail hereinafter. Such aspects may, however, be embodied in many different forms and should not be construed as limited to the embodiments set forth herein; rather, these embodiments are provided so that this disclosure will be thorough and complete, and will fully convey its scope to those skilled in the art. For convenience, certain terms employed in the specification, examples, and claims are collected here. Unless defined otherwise, all technical and scientific terms used in this disclosure have the same meanings as commonly understood by one of ordinary skill in the art to which this disclosure belongs.

Where a range of values is provided, it is intended that each intervening value between the upper and lower limit of that range and any other stated or intervening value in that stated range is encompassed within the disclosure. For example, if a range of 1 wt % to 8 wt % is stated, it is intended that 2 wt %, 3 wt %, 4 wt %, 5 wt %, 6 wt %, and 7 wt % are also explicitly disclosed, as well as the range of values greater than or equal to 1 wt % and the range of values less than or equal to 8 wt %.

All percentages, parts and ratios are based upon the total weight of the formulations and compositions and all measurements made are at about 25° C., unless otherwise specified.

It must be noted that as used herein and in the appended claims, the singular forms "a", "an", and "the" include plural reference unless the context clearly dictates otherwise. As well, the terms "a" or "an", "one or more" and "at least one" can be used interchangeably herein.

As used herein, the term "about" means plus or minus 10% of the numerical value of the number with which it is being used. Therefore, about 50% means in the range of 45%-55%.

The term "administer" or other forms of administer, such as "administering" and "administration," as used herein refers to directly administering a nutritional composition to a subject, typically orally or through feeding.

The term "algorithm" is used to describe design processes or analytical methods that may consist of a specific sequence of steps, rules, and/or computation.

The term "ameliorate" or other forms of ameliorate, such as "ameliorating," is meant to administer a dietary supplement disclosed herein or to perform a method disclosed herein in order to reduce or improve a particular characteristic or event (e.g., aging or neurodegenerative disease); such term is also used in the context of reducing existing intake inadequacies of beneficial nutrients in a subject by increasing the intake of such nutrients.

The transitional term "comprising," which is synonymous with "including," "containing," or "characterized by," is inclusive or open-ended and does not exclude additional, un-recited elements or method steps. By contrast, the transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed subject matter. In some embodiments or claims where the term comprising is used as the transition phrase, such embodiments can also be envisioned with replacement of the term "comprising" with the terms "consisting of" or "consisting essentially of."

The term "derivative," used in the context of describing a compound or nutrient (e.g. "myricetin or derivative thereof") refers to a chemical or biochemical modification, isomer, or analog of such molecule. The term "derivative" includes glycosides or other conjugated forms of the compound or nutrient typically found in nature or as a result of extraction or purification processes. For simplicity and clarity, "derivative" may also include the free form or aglycone form of a compound or nutrient.

As used herein, the term "dietary component" refers to a food, food product, or food group.

As used herein, "DRI" refers to the Dietary Reference Intakes issued by the Food and Nutrition Board of the Institute of Medicine, National Academy of Sciences. DRI is the general term for a set of reference values used to plan and assess nutrient intakes of healthy people. These values, which vary by age and gender, include: Recommended Dietary Allowance (RDA): average daily level of intake sufficient to meet the nutrient requirements of nearly all (97%-98%) healthy people; Adequate Intake (AI): established when evidence is insufficient to develop an RDA and is set at a level assumed to ensure nutritional adequacy; and Tolerable Upper Intake Level (UL): maximum daily intake unlikely to cause adverse health effects.

The term "dietary supplement" refers to any combination of compounds or micronutrients that can be administered to or taken by a subject to provide, supply, or increase the levels of vitamins, minerals, essential trace elements, amino acids, peptides, nucleic acids, oligonucleotides, lipids, cholesterols, steroids, carbohydrates, and combinations thereof. "Dietary supplement" is to be interpreted as meaning any substance, extract, or mixture of substances that: may supplement the human diet; is a concentrated source of a vitamin or mineral or other substances with a nutritional or physiological effect, alone or in combination; is taken orally as a powder, pill, capsule, tablet, food, or liquid. "Dietary supplement" offers health benefits, including reduction in the risk of a disease or health-related condition, provides a structure/function claim, or provides a nutrient claim. The term "dietary supplement" includes the definition of dietary supplements as stated by the US Food and Drug Administration (FDA), according to the Dietary Supplement Health and Education Act (DSHEA) of 1994: a dietary supplement is a product taken by mouth that contains a "dietary ingredient" intended to supplement the diet, whereas the "dietary ingredients" in these products may include vitamins, minerals, herbs or other botanicals, amino acids, and substances such as enzymes, organ tissues, glandulars, and metabolites. Per FDA, dietary supplements can also be extracts or concentrates and may be found in many forms, such as tablets, capsules, softgels, gelcaps, liquids, or powders.

An "effective amount" of a nutritional composition is a predetermined amount calculated to achieve the desired effect, e.g., to maintain or support brain health or to prevent, reduce risk of, inhibit, block, or reverse the effect of neurodegenerative disease or decline in mental or cognitive qualities. The activity contemplated by the present methods includes maintenance or support of health, maintenance or support of structure or function at the cellular, tissue, or whole body levels, reduction of risk of disease, and both medical treatment and/or prophylactic treatment, as appropriate. The specific dose of a nutritional composition administered, according to the embodiments described herein, to obtain such effects will, of course, be determined by the particular circumstances surrounding the case. The desired effect may be demonstrated by any of the following alone or in combination: maintained or enhanced brain function or mental or cognitive qualities, comprising measures of cognitive ability, concentration, mental acuity, mental alertness, cognitive well-being, mental performance, memory, mental sharpness, mental vitality, mental clarity, short term memory, learning, brain health, psychological well-being, or reduction of risk, prevention, or delay of neurodegenerative disease.

The term "epidemiological" or other forms of epidemiological, such as "epidemiology," may be used interchangeably with forms of the terms "observational" or "community-based." Such terms are used in the context of describing studies, evidence, data, results, or other terms that may imply analyses.

The term "flavonoids" refers to bioactive molecules that are classified as flavonoids, comprising the sub-groups anthocyanidins, flavan-3-ols, flavanones, flavones, and flavonols, whether in aglycone, glycoside, or otherwise conjugated forms.

The term "improve" or other forms of improve, such as "improving" or "improvement," as used herein refers to the ability of the dietary supplement to make the subject better or healthier, e.g. to increase a subject's mental capacity or memory or increase levels of biomolecules or biomarkers to beneficial or optimal levels.

The terms "maintain" or other forms of maintain, such as "maintenance" or "maintaining," and "support" or other forms of support, such as "supporting," as used herein refer to the ability of the dietary supplement to provide the necessary levels of nutrients to promote health and wellness, to keep steady-state levels, or to attain optimal levels of nutrients, biomolecules, or biomarkers to support health in the subject's cells and tissues; such terms also refer to the ability of the dietary supplement to provide the necessary levels of nutrients to promote relevant molecular mechanisms of action (MOA), structure, and/or function at the cellular, tissue, or whole body levels for the subject. The effect of such maintenance or support may include promotion and sustainment of brain health and wellness, reduced risk of neurodegenerative disease or neuropathology, or delayed onset or prevention of neurodegenerative disease or neuropathology.

The terms "neuroprotection" or "neuroprotective" generally describe a benefit to brain health, which can include the maintenance and/or support of normal or optimal brain function or cognitive qualities, as well as reduction of risk, delay of onset, slowing, protection and/or prevention of neurodegenerative diseases, neuropathologies, or cognitive decline.

The terms "nutrient" and "micronutrient" are used interchangeably, and they refer to nutritional compounds, such as lettered vitamins, minerals, and polyphenolic compounds, such as flavonoids, which may be used as ingredients in a dietary supplement composition.

The terms "polyphenolic" or "polyphenolic compound" refer broadly to phytochemicals related to human health, which include flavonoids, carotenoids, phytosterols, and other biologically active (bioactive) compounds typically found in plants.

The term "protect" or other forms of protect, such as "protecting" or "protective," includes the administration of the dietary supplement described herein to reduce risk of disease, prevent or delay the onset of the symptoms of disease, delay or decrease the progression of a disease and/or its symptoms, slow aging-related mental or general brain decline, or generally prevent a disease, condition, or disorder; "protect" or its other forms also refers to the ability of the dietary supplement to provide the necessary levels of nutrients to promote normal, healthy molecular mechanisms of action (MOA), structure, and/or function at the cellular, tissue, or whole body levels for the subject, which may maintain brain health.

The term "prevent" or other forms of prevent, such as "preventing" or "prevention," is meant to stop a particular event or characteristic, to stabilize or delay the development or progression of a particular event or characteristic, or to minimize the chances that a particular event or characteristic will occur. Prevention does not require comparison to a control as it is typically more absolute than, for example, reduce or lower.

The terms "reduces" or "lowers," or other forms of the words, such as "reducing," "reduction," or "lowering," refer to a decrease in an event, characteristic, or symptom.

The terms "slow" or "slowing" as used herein refers to the ability of the dietary supplement to inhibit the progression of age-related mental decline, general brain decline, or neurodegeneration.

As used herein, the use of the term "subject" refers to an individual. "Subject" includes a mammal, such as a primate or a human.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual components, compounds, nutrients, or groups thereof, or any members of a claimed group, less than the full measure of this disclosure can be claimed for any reason.

Throughout this disclosure, various patents, patent applications, and publications may be referenced. The disclosures of these patents, patent applications, and publications in their entireties are incorporated into this disclosure by reference in order to more fully describe the state of the art as known to those skilled therein as of the date of this disclosure. This disclosure will govern in the instance that there is any inconsistency between the patents, patent applications, and publications cited and this disclosure.

Dietary Supplement Compositions

Dietary supplement compositions described herein are designed to assist subjects in achieving the nutrient intake profiles of neuroprotective dietary patterns. As previously mentioned, only recently has scientific research formally identified and begun validating specific dietary patterns as neuroprotective, including the Mediterranean diet and MIND diet. Typically, the means by which a subject achieves such neuroprotective dietary patterns is through the choice and preparation of food groups that the subject consumes (e.g. combination of vegetables, fruits, nuts, seeds, fish, and other foods), i.e. through careful grocery shopping and cooking specific recipes that follow such dietary patterns. In the marketplace today, some dietary supplement products may typically provide one or a subset of nutrients relevant to the brain, but they are not designed specifically with intent to complement neuroprotective dietary patterns in a coherent and comprehensive manner; this is due to the difficulty in analyzing the breadth and depth of data in nutritional and scientific research to identify specific combinations of nutrients that are most brain-relevant from such dietary patterns. To advance the art, herein are described novel dietary supplement compositions that are specifically, systematically, and comprehensively designed to complement a subject's diet to assist that subject in achieving a neuroprotective dietary pattern. Such dietary supplement compositions are constructed using the MeDi, MIND, DASH, a posteriori, or composite dietary patterns linked to neuroprotection as the governing basis for nutrient identification, evaluation, and selection. Such dietary supplement compositions are made up of unique combinations of nutrients for which intake inadequacies are deepest. Such dietary supplement compositions comprise six component groupings, described as follows.

Embodiments disclosed herein are directed to dietary supplements comprising a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

In certain embodiments, vitamin B1 is present as thiamine in water-soluble form, selected from the group consisting of thiamin mononitrate, thiamin hydrochloride, and combinations thereof. The U.S. Recommended Daily Allowance (RDA) for vitamin B1 in the form of thiamin is 1.2 mg/day for adult males and 1.1 mg/day for adult females. In certain embodiments, vitamin B1 is in an amount selected from the group consisting of about 1 mg/day to about 10 mg/day, about 2 mg/day to about 9 mg/day, about 3 mg/day to about 8 mg/day, about 4 mg/day to about 7 mg/day, and about 5 mg/day to about 6 mg/day. In certain embodiments, vitamin B1 is in an amount of about 5 mg/day.

In certain embodiments, vitamin B2 is present in a form selected from the group consisting of riboflavin, riboflavin 5' phosphate, and combinations thereof. The U.S. RDA for vitamin B2 in the form of riboflavin is 1.3 mg/day for adult males and 1.1 mg/day for adult females. In certain embodiments, vitamin B2 is in an amount selected from the group consisting of about 2 mg/day to about 100 mg/day, about 4 mg/day to about 80 mg/day, about 6 mg/day to about 60 mg/day, about 8 mg/day to about 40 mg/day, and about 10 mg/day to about 20 mg/day. In certain embodiments, vitamin B2 is in an amount of about 20 mg/day. In certain embodiments, riboflavin is in an amount of about 2 mg/day to about 100 mg/day. In certain embodiments, riboflavin 5' phosphate is in an amount of about 2 mg/day to about 100 mg/day. In certain embodiments, riboflavin 5' phosphate is in an amount of about 20 mg/day.

In certain embodiments, vitamin B3 is present in a form selected from the group consisting of nicotinamide, niacin, nicotinamide riboside, and combinations thereof. The U.S. RDA for vitamin B3 in the form of niacin is 16 mg/day for adult males and 14 mg/day for adult females. In certain embodiments, vitamin B3 is in an amount selected from the group consisting of about 25 mg/day to about 250 mg/day, about 30 mg/day to about 225 mg/day, about 40 mg/day to about 200 mg/day, about 45 mg/day to about 175 mg/day, and about 50 mg/day to about 150 mg/day. In certain embodiments, vitamin B3 is in an amount of about 50 mg/day. At higher dosages, nicotinamide would be the preferred form of vitamin B3 to avoid skin flushing side effects associated with high doses of niacin. In certain embodiments, nicotinamide is in an amount of about 25 mg/day to about 250 mg/day. In certain embodiments, nicotinamide is in an amount of about 50 mg/day. In certain embodiments, niacin is in an amount of about 25 mg/day to about 250 mg/day.

In certain embodiments, vitamin B6 is present in a form selected from the group consisting of pyridoxine, pyridoxal, pyridoxamine, pyridoxal 5'-phosphate, pyridoxine 5'-phosphate, pyridoxamine 5'-phosphate, and combinations thereof. The U.S. RDA for vitamin B6 is 1.3 mg/day for adult males and adult females up to the age of 50 years. The U.S. RDA for vitamin B6 is 1.7 mg/day for adult males and 1.5 mg/day for adult females greater than 50 years old. In certain embodiments, vitamin B6 is in an amount selected from the group consisting of about 1 mg/day to about 50 mg/day, about 2 mg/day to about 40 mg/day, about 3 mg/day to about 30 mg/day, about 4 mg/day to about 20 mg/day, and about 5 mg/day to about 10 mg/day. In certain embodiments, vitamin B6 is in an amount of about 5 mg/day. In certain embodiments, pyridoxine is in an amount of about 1 mg/day to about 50 mg/day. In certain embodiments, pyridoxine is in an amount of about 5 mg/day.

In certain embodiments, vitamin B9 is present in a form selected from the group consisting of folic acid, folate, 5-methyltetrahydrofolate, and combinations thereof. The U.S. RDA for vitamin B9 is 400 µg/day (in dietary folate equivalents) for adult males and adult females. In certain embodiments, vitamin B9 is in an amount selected from the group consisting of about 100 µg/day to about 1000 µg/day, about 150 µg/day to about 900 µg/day, about 200 µg/day to about 800 µg/day, about 250 µg/day to about 700 µg/day, and about 300 µg/day to about 600 µg/day. In certain embodiments, vitamin B9 is in an amount of about 400 µg/day. In certain embodiments, 5-methyltetrahydrofolate is in an amount of about 100 µg/day to about 1000 µg/day. In certain embodiments, 5-methyltetrahydrofolate is in an amount of about 400 µg/day.

In certain embodiments, vitamin B12 is present in a form selected from the group consisting of cobalamin, cyanocobalamin, methylcobalamin, adenosylcobalamin, hydroxocobalamin, an analog thereof, and combinations thereof. The U.S. RDA for vitamin B12 is 2.4 µg/day for adult males and adult females. In certain embodiments, vitamin B12 is in an amount selected from the group consisting of about 10 µg/day to about 1000 µg/day, about 15 µg/day to about 900 µg/day, about 20 µg/day to about 800 µg/day, about 25 µg/day to about 700 µg/day, about 30 µg/day to about 600 µg/day, about 35 µg/day to about 500 µg/day, about 40 µg/day to about 400 µg/day, and about 45 µg/day to about 300 µg/day. In certain embodiments, vitamin B12 is in an amount of about 1000 µg/day. In certain embodiments, hydroxocobalamin is in an amount of about 1000 µg/day. In certain embodiments, vitamin B12 is in an amount of about 20 µg/day. In certain embodiments, hydroxocobalamin is in an amount of about 20 µg/day.

In certain embodiments, vitamin C is present in a form selected from the group consisting of ascorbic acid, ascorbate (including sodium or calcium ascorbates), and combinations thereof. The U.S. RDA for vitamin C is 90 mg/day for adult males and 75 mg/day for adult females. In certain embodiments, vitamin C is in an amount selected from the group consisting of about 30 mg/day to about 400 mg/day, about 35 mg/day to about 350 mg/day, about 40 mg/day to about 300 mg/day, about 45 mg/day to about 250 mg/day, and about 50 mg/day to about 200 mg/day. In certain embodiments, vitamin C is in an amount of about 60 mg/day. In certain embodiments, an ascorbate is in an amount of about 30 mg/day to about 400 mg/day. In certain embodiments, an ascorbate is in an amount of about 60 mg/day.

In certain embodiments, vitamin D is present in a form selected from the group consisting of ergocalciferol, cholecalciferol, and combinations thereof. The U.S. RDA for vitamin D is 15 µg/day for adult males and adult females up to the age of 70 years. The U.S. RDA for vitamin D is 20 µg/day for adult males and adult females greater than 70 years old. In certain embodiments, vitamin D is in an amount selected from the group consisting of about 20 µg/day to about 100 µg/day, about 25 µg/day to about 90 µg/day, about 30 µg/day to about 85 µg/day, about 35 µg/day to about 70 µg/day, about 40 µg/day to about 65 µg/day, about 45 µg/day to about 60 µg/day, and about 50 µg/day to about 55 µg/day. In certain embodiments, vitamin D is in an amount of about 100 µg/day. In certain embodiments, cholecalciferol is in an amount of about 20 µg/day to about 100 µg/day. In certain embodiments, cholecalciferol is in an amount of about 30 µg/day.

In certain embodiments, vitamin K is present in a form selected from the group consisting of phylloquinone, phytonadione, menaquinone, and combinations thereof. The U.S. AI for vitamin K is 120 µg/day for adult males and 90 µg/day for adult females. In certain embodiments, vitamin K is in an amount selected from the group consisting of about 50 µg/day to about 5000 µg/day, about 75 µg/day to about 4000 µg/day, about 100 µg/day to about 3000 µg/day, about 125 µg/day to about 2000 µg/day, about 150 µg/day to about 1000 µg/day, about 175 µg/day to about 500 µg/day, and about 200 µg/day to about 300 µg/day. In certain embodiments, vitamin K is in an amount of about 250 µg/day. In certain embodiments, phylloquinone is in an amount of about 50 µg/day to about 5000 µg/day. In certain embodiments, phylloquinone is in an amount of about 250 µg/day.

In certain embodiments, vitamin E is present in a form selected from the group consisting of alpha-tocopherol, d-alpha-tocopherol (RRR-alpha-tocopherol), alpha-tocopherol ester, gamma-tocopherol, and combinations thereof. The U.S. RDA for vitamin E in the form of alpha-tocopherol is 15 mg/day for adult males and adult females. In certain embodiments, alpha-tocopherol, d-alpha-tocopherol (RRR-alpha-tocopherol) or alpha-tocopherol ester is in an amount selected from the group consisting of about 15 mg/day to about 250 mg/day, about 20 mg/day to about 200 mg/day, about 30 mg/day to about 175 mg/day, about 40 mg/day to about 150 mg/day, about 20 mg/day to about 100 mg/day, and about 50 mg/day to about 100 mg/day. In certain embodiments, alpha-tocopherol is in an amount of about 20 mg/day. In certain embodiments, gamma-tocopherol is in an amount selected from the group consisting of about 15 mg/day to about 1250 mg/day, about 20 mg/day to about 1000 mg/day, about 30 mg/day to about 875 mg/day, about 40 mg/day to about 750 mg/day, and about 50 mg/day to about 500 mg/day. In certain embodiments, alpha-tocopherol is in an amount of about 40 mg/day. The presence of gamma-tocopherol in the composition is intended to prevent the depletion of gamma-tocopherol in the body when alpha-tocopherol is supplemented and to work synergistically with alpha-tocopherol to raise levels of both tocopherols in the body. In certain embodiments, the ratio of gamma-tocopherol:alpha-tocopherol is about 5:1, about 4:1, about 3:1, about 2:1, or about 1:1. In certain embodiments, the ratio of gamma-tocopherol:alpha-tocopherol is about 2:1. In certain embodiments, d-alpha-tocopherol is in an amount of about 15 mg/day to about 250 mg/day. In certain embodiments, alpha-tocopherol is in an amount of about 20 mg/day. In certain embodiments, gamma-tocopherol is in an amount of about 40 mg/day.

In certain embodiments, vitamin B1 is present as thiamine in oil-soluble form, selected from the group consisting of benfotiamine, allithiamine, fursultiamine, sulbutiamine, and combinations thereof. The U.S. RDA for vitamin B1 in the form of thiamin is 1.2 mg/day for adult males and 1.1 mg/day for adult females. In certain embodiments, vitamin B1 is in an amount selected from the group consisting of about 1 mg/day to about 10 mg/day, about 2 mg/day to about 9 mg/day, about 3 mg/day to about 8 mg/day, about 4 mg/day to about 7 mg/day, and about 5 mg/day to about 6 mg/day. In certain embodiments, vitamin B1 is in an amount of about 5 mg/day. In certain embodiments, benfotiamine is in an amount of about 1 mg/day to about 10 mg/day. In certain embodiments, benfotiamine is in an amount of about 5 mg/day.

In certain embodiments, magnesium is present in a form selected from the group consisting of sulfate, 1-threonate, glycinate, citrate, lactate, oxide, chloride, gluconate, malate, acetyl taurate, a magnesium conjugate, a magnesium derivative, and combinations thereof. The U.S. RDA for magnesium (in elemental form) is 420 mg/day for adult males and 320 mg/day for adult females. In certain embodiments, magnesium is in an amount selected from the group consisting of about 25 mg/day to about 400 mg/day, about 30 mg/day to about 350 mg/day, about 35 mg/day to about 300 mg/day, about 40 mg/day to about 250 mg/day, about 45 mg/day to about 200 mg/day, and about 50 mg/day to about 150 mg/day. In certain embodiments, magnesium is in an amount of about 50 mg/day.

In certain embodiments, the primary polyphenolic compound is present as myricetin or derivative thereof (which herein refers to forms such as myricetin aglycone, free myricetin, myricetin glycoside, myricetin derivative, or combinations thereof), kaempferol or derivative thereof (which herein refers to forms such as kaempferol aglycone, free kaempferol, kaempferol glycoside, kaempferol derivative, or combinations thereof), quercetin or derivative thereof (which herein refers to forms such as quercetin aglycone, free quercetin, quercetin glycoside, quercetin derivative, or combinations thereof), isorhamnetin or derivative thereof (which herein refers to forms such as isorhamnetin aglycone, free isorhamnetin, isorhamnetin glycoside, isorhamnetin derivative, or combinations thereof), or combinations thereof. In certain embodiments, the primary polyphenolic compound is in an amount selected from the group consisting of about 1 mg/day to about 800 mg/day, about 1 mg/day to about 100 mg/day, about 2 mg/day to about 200 mg/day, about 10 mg/day to about 400 mg/day, about 15 mg/day to about 125 mg/day, about 20 mg/day to about 100 mg/day, and about 30 mg/day to about 50 mg/day. In certain embodiments, the primary polyphenolic compound is in an amount of about 10 mg/day. In certain embodiments, the primary polyphenolic compound is in an amount of about 20 mg/day. In certain embodiments, the primary polyphenolic compound is in an amount of about 50 mg/day. In certain embodiments, myricetin or derivative thereof is in an amount of about 1 mg/day to about 100 mg/day. In certain embodiments, myricetin or derivative thereof is in an amount of about 10 mg/day. In certain embodiments, kaempferol or derivative thereof is in an amount of about 2 mg/day to about 200 mg/day. In certain embodiments, kaempferol or derivative thereof is in an amount of about 20 mg/day. In certain embodiments, quercetin or derivative thereof is in an amount of about 10 mg/day to about 400 mg/day. In certain embodiments, quercetin or derivative thereof is in an amount of about 50 mg/day. In certain embodiments, isorhamnetin or derivative thereof is in an amount of about 1 mg/day to about 100 mg/day. In certain embodiments, isorhamnetin or derivative thereof is in an amount of about 2 mg/day.

In certain embodiments, the ratio of kaempferol or derivative thereof:myricetin or derivative thereof is about 2:1 to about 5:1, about 3:1 to about 5:1 or about 4:1 to about 5:1. In certain embodiments, the ratio of quercetin or derivative thereof:kaempferol or derivative thereof is about 2:1 to about 6:1, about 3:1 to about 6:1, about 4:1 to about 6:1, or about 5:1 to about 6:1.

In certain embodiments, any one or more components of the primary polyphenolic compound may be at a purity selected from the group consisting of greater than 85%, greater than 90%, and greater than 95%. In certain embodiments, the primary polyphenolic compound is at a purity greater than 90%.

In certain embodiments, the primary polyphenolic compound is present in the composition as the combination of myricetin or derivative thereof, kaempferol or derivative thereof, and quercetin or derivative thereof. In certain embodiments, the primary polyphenolic compound is present in the composition as the combination of myricetin or derivative thereof, kaempferol or derivative thereof, quercetin or derivative thereof, and isorhamnetin or derivative thereof.

In certain embodiments, the secondary polyphenolic compound is present as pelargonidin or derivative thereof (which herein refers to forms such as pelargonidin aglycone, free pelargonidin, pelargonidin glycoside, pelargonidin derivative, or combinations thereof), malvidin or derivative thereof (which herein refers to forms such as malvidin aglycone, free malvidin, malvidin glycoside, malvidin derivative, or combinations thereof), cyanidin or derivative thereof (which herein refers to forms such as cyanidin aglycone, free cyanidin, cyanidin glycoside, cyanidin derivative, or combinations thereof), delphinidin or derivative thereof (which herein refers to forms such as delphinidin aglycone, free delphinidin, delphinidin glycoside, delphinidin derivative, or combinations thereof), lutein or derivative thereof (which herein refers to forms such as lutein, lutein derivative, or combinations thereof; for clarity, lutein also refers to zeaxanthin, an isomer of lutein, and its derivatives), resveratrol or derivative thereof (which herein refers to forms such as resveratrol aglycone, free resveratrol, resveratrol glycoside, resveratrol derivative, or combinations thereof), pterostilbene or derivative thereof (which herein refers to forms such as pterostilbene aglycone, free pterostilbene, pterostilbene glycoside, pterostilbene derivative, or combinations thereof), a catechin composition (as described below), or combinations thereof. In certain embodiments, the secondary polyphenolic compound is in an amount selected from the group consisting of 0.01 mg/day to about 2000 mg/day, about 0.025 mg/day to about 5 mg/day, about 0.5 mg/day to about 1500 mg/day, about 1 mg/day to about 500 mg/day, about 1 mg/day to about 1000 mg/day, about 2 mg/day to about 50 mg/day, about 2 mg/day to about 150 mg/day, about 5 mg/day to about 300 mg/day, about 5 mg/day to about 500 mg/day, about 10 mg/day to about 100 mg/day, about 10 mg/day to about 400 mg/day, about 15 mg/day to about 500 mg/day, about 10 mg/day to about 100 mg/day, and about 40 mg/day to about 1500 mg/day. In certain embodiments, the secondary polyphenolic compound is in an amount of about 5 mg/day. In certain embodiments, pelargonidin or derivative thereof is in an amount of about 2 mg/day to about 150 mg/day. In certain embodiments, malvidin or derivative thereof is in an amount of about 10 mg/day to about 400 mg/day. In certain embodiments, cyanidin or derivative thereof is in an amount of about 15 mg/day to about 500 mg/day. In certain embodiments, delphinidin or derivative thereof is in an amount of about 5 mg/day to about 300 mg/day. In certain embodiments, lutein or derivative thereof is in an amount of about 2 mg/day to about 50 mg/day. In certain embodiments, resveratrol or derivative thereof is in an amount of about 1 mg/day to about 500 mg/day. In certain embodiments, pterostilbene or derivative thereof is in an amount of about 0.025 mg/day to about 5 mg/day. In certain embodiments, the catechin composition is in an amount of about 40 mg/day to about 1500 mg/day.

In certain embodiments, the ratio of lutein:zeaxanthin is from about 5:1 to about 10:1, about 6:1 to about 10:1, about 7:1 to about 10:1, about 8:1 to about 10:1, or about 9:1 to about 10:1.

The catechin composition comprises catechins typically found in green tea (*Camellia sinensis*). In certain embodiments, the catechin composition comprises epigallocatechin gallate (EGCG) in an amount of about 30 mg/day to about 500 mg/day. In certain embodiments, the ratio of EGCG:total catechins is from about 1:4 to about 3:4 (e.g. a catechin composition with 50 mg of EGCG and 150 mg of total catechins would have a EGCG:total catechins ratio of 1:3), wherein the amount of total catechins is the sum of all catechins including EGCG, epigallocatechin (EGC), epicatechin gallate (ECG), and epicatechin (EC). In certain embodiments, the catechin composition comprises l-theanine. In certain embodiments, l-theanine is in a ratio with the total catechins, wherein the ratio of the total catechins:l-theanine is from about 2:1 to about 8:1.

In certain embodiments, any one or more components of the secondary polyphenolic compound may be present at a purity selected from the group consisting of greater than 85%, greater than 90%, and greater than 95%. In certain embodiments, the secondary polyphenolic compound is at a purity greater than 90%.

In certain embodiments, the omega-3-phospholipid complex is selected from the group consisting of phospholipid forms of DHA, EPA, and combinations thereof. In certain embodiments, the phospholipid forms of DHA and EPA are complexes including compounds selected from the group consisting of phosphatidylserine, phosphatidylcholine, phosphatidylethanolamine, lysophosphatidylserine, lysophosphatidylcholine, lysophosphatidylethanolamine, and combinations thereof. In certain embodiments, the omega-3-phospholipid complex includes DHA in an amount of about 70 mg/day to about 2000 mg/day. In certain embodiments, the omega-3-phospholipid complex includes EPA in an amount of about 18 mg/day to about 2000 mg/day. In certain embodiments, the ratio of DHA:EPA is about 1:1 to about 4:1. In certain embodiments, the omega-3-phospholipid complex includes DHA in an amount of about 200 mg/day and EPA in an amount of about 60 mg/day.

In certain embodiments, a dietary supplement composition comprises a water-soluble vitamin component, an oil-soluble vitamin component, about 25 mg/day to about 400 mg/day magnesium or derivatives thereof, a primary polyphenolic compound, a secondary polyphenolic compound, and an omega-3-phospholipid complex; wherein the water-soluble vitamin component is selected from the group consisting of vitamin B1 (water soluble form) in an amount of about 1 mg/day to about 10 mg/day, vitamin B2 in an amount of about 2 mg/day to about 100 mg/day, vitamin B3 in an amount of about 25 mg/day to about 250 mg/day, vitamin B6 in an amount of about 1 mg/day to about 50 mg/day, vitamin B9 in an amount of about 100 μg/day to about 1000 μg/day, vitamin B12 in an amount of about 10 μg/day to about 1000 μg/day, vitamin C in an amount of about 30 mg/day to about 400 mg/day, and combinations thereof; wherein the oil-soluble vitamin component is selected from the group consisting of vitamin D in an amount of about 20 μg/day to about 100 μg/day, vitamin K in an amount of about 50 μg/day to about 5000 μg/day, alpha-tocopherol in an amount of about 15 mg/day to about 250 mg/day, gamma-tocopherol in an amount of about 15 mg/day to about 1250 mg/day, vitamin B1 (oil soluble form) in an amount of about 1 mg/day to about 10 mg/day, and combinations thereof; wherein the primary polyphenolic compound is selected from the group consisting of myricetin or derivative thereof in an amount of about 1 mg/day to about 100 mg/day, kaempferol or derivative thereof in an amount of about 2 mg/day to about 200 mg/day, quercetin or derivative thereof in an amount of about 10 mg/day to about 400 mg/day, isorhamnetin or derivative thereof in an amount of about 1 mg/day to about 100 mg/day, and combinations thereof; wherein the secondary polyphenolic compound is selected from the group consisting of pelargonidin or derivative thereof in an amount of about 2 mg/day to about 150 mg/day, malvidin or derivative thereof in an amount of about 10 mg/day to about 400 mg/day, cyanidin or derivative thereof in an amount of about 15 mg/day to about 500 mg/day, delphinidin or derivative thereof in an amount of about 5 mg/day to about 300 mg/day, lutein or derivative thereof in an amount of about 2 mg/day to about 50 mg/day, resveratrol or derivative thereof in an amount of about 1 mg/day to about 500 mg/day, pterostilbene or derivative thereof in an amount of about 0.025 mg/day to about 5 mg/day, and combinations thereof; and wherein an omega-3-phospholipid complex includes DHA in an amount of about 70 mg/day to about 2000 mg/day and EPA in an amount of about 18 mg/day to about 2000 mg/day.

In certain embodiments, a dietary supplement comprises water-soluble thiamin, riboflavin, nicotinamide, cobalamin, cholecalciferol, phylloquinone, alpha-tocopherol, gamma-tocopherol, benfotiamine, magnesium, myricetin, kaempferol, quercetin, isorhamnetin, pelargonidin, malvidin, cyanidin, delphinidin, lutein, and resveratrol. In certain embodiments, the dietary supplement comprises a derivative of one or more component.

In certain embodiments, a dietary supplement comprises about 1 mg/day to about 10 mg/day of water-soluble thiamin, about 2 mg/day to about 100 mg/day of riboflavin, about 25 mg/day to about 250 mg/day of nicotinamide, about 10 μg/day to about 1000 μg/day of cobalamin, about 2 μg/day to about 100 μg/day of cholecalciferol, about 50 μg/day to about 5000 μg/day of phylloquinone, about 15 mg/day to about 250 mg/day of alpha-tocopherol, about 15 mg/day to about 1250 mg/day of gamma-tocopherol, about 1 mg/day to about 10 mg/day of benfotiamine, about 25 mg/day to about 400 mg/day of magnesium, about 1 mg/day to about 100 mg/day of myricetin, about 2 mg/day to about 200 mg/day of kaempferol, about 10 mg/day to about 400 mg/day of quercetin, about 1 mg/day to about 100 mg/day of isorhamnetin, about 5 mg/day to about 150 mg/day of pelargonidin, about 10 mg/day to about 400 mg/day of malvidin, about 15 mg/day to about 500 mg/day of cyanidin, about 5 mg/day to about 300 mg/day of delphinidin, about 2 mg/day to about 50 mg/day of lutein, and about 1 mg/day to about 500 mg/day of resveratrol. In certain embodiments, the dietary supplement comprises a derivative of one or more component.

In certain embodiments, a dietary supplement comprises about 5 mg/day of water-soluble thiamin, about 20 mg/day of riboflavin, about 50 mg/day of nicotinamide, about 1000 μg/day of cobalamin, about 35 μg/day of cholecalciferol, about 250 μg/day of phylloquinone, about 20 mg/day of alpha-tocopherol, about 40 mg/day of gamma-tocopherol, about 5 mg/day of benfotiamine, about 70 mg/day of magnesium, about 10 mg/day of myricetin, about 30 mg/day of kaempferol, about 100 mg/day of quercetin, about 5 mg/day of isorhamnetin, about 15 mg/day of pelargonidin, about 60 mg/day of malvidin, about 80 mg/day of cyanidin, about 5 mg/day of delphinidin, about 5 mg/day of lutein, and about 20 mg/day of resveratrol. In certain embodiments, the dietary supplement comprises a derivative of one or more component.

In certain embodiments, a dietary supplement comprises riboflavin, nicotinamide, cobalamin, cholecalciferol, alpha-tocopherol, gamma-tocopherol, benfotiamine, magnesium, myricetin, kaempferol, quercetin, and malvidin. In certain embodiments, the dietary supplement comprises a derivative of one or more component.

In certain embodiments, a dietary supplement comprises about 2 mg/day to about 100 mg/day of riboflavin, about 25 mg/day to about 250 mg/day of nicotinamide, about 10 μg/day to about 1000 μg/day of cobalamin, about 20 μg/day to about 100 μg/day of cholecalciferol, about 15 mg/day to about 250 mg/day of alpha-tocopherol, about 15 mg/day to about 1250 mg/day of gamma-tocopherol, about 1 mg/day to about 10 mg/day of benfotiamine, about 25 mg/day to about 400 mg/day of magnesium, about 1 mg/day to about 100 mg/day of myricetin, about 2 mg/day to about 200 mg/day of kaempferol, about 10 mg/day to about 400 mg/day of quercetin, and about 10 mg/day to about 400 mg/day of malvidin. In certain embodiments, the dietary supplement comprises a derivative of one or more component.

In certain embodiments, a dietary supplement comprises about 20 mg/day of riboflavin, about 50 mg/day of nicotinamide, about 1000 μg/day of cobalamin, about 35 μg/day of cholecalciferol, about 20 mg/day of alpha-tocopherol, about 40 mg/day of gamma-tocopherol, about 5 mg/day of benfotiamine, about 70 mg/day of magnesium, about 10 mg/day of myricetin, about 30 mg/day of kaempferol, about 100 mg/day of quercetin, and about 60 mg/day of malvidin. In certain embodiments, the dietary supplement comprises a derivative of one or more component.

In certain embodiments, the dietary supplement comprises riboflavin, nicotinamide, cobalamin, cholecalciferol, alpha-tocopherol, gamma-tocopherol, benfotiamine, magnesium, myricetin, kaempferol, quercetin, and isorhamnetin. In certain embodiments, the dietary supplement comprises a derivative of one or more component.

In certain embodiments, a dietary supplement comprises about 2 mg/day to about 100 mg/day of riboflavin, about 25 mg/day to about 250 mg/day of nicotinamide, about 10

μg/day to about 1000 μg/day of cobalamin, about 20 μg/day to about 100 μg/day of cholecalciferol, about 15 mg/day to about 250 mg/day of alpha-tocopherol, about 15 mg/day to about 1250 mg/day of gamma-tocopherol, about 1 mg/day to about 10 mg/day of benfotiamine, about 25 mg/day to about 400 mg/day of magnesium, about 1 mg/day to about 100 mg/day of myricetin, about 2 mg/day to about 200 mg/day of kaempferol, about 10 mg/day to about 400 mg/day of quercetin, and about 1 mg/day to about 100 mg/day of isorhamnetin. In certain embodiments, the dietary supplement comprises a derivative of one or more component.

In certain embodiments, a dietary supplement comprises about 20 mg/day of riboflavin, about 50 mg/day of nicotinamide, about 1000 μg/day of cobalamin, about 35 μg/day of cholecalciferol, about 20 mg/day of alpha-tocopherol, about 40 mg/day of gamma-tocopherol, about 5 mg/day of benfotiamine, about 70 mg/day of magnesium, about 10 mg/day of myricetin, about 30 mg/day of kaempferol, about 100 mg/day of quercetin, and about 5 mg/day of isorhamnetin. In certain embodiments, the dietary supplement comprises a derivative of one or more component.

In certain embodiments, a dietary supplement comprises riboflavin 5' phosphate, nicotinamide, methylcobalamin, cholecalciferol, phylloquinone, alpha-tocopherol, gamma-tocopherol, benfotiamine, magnesium, myricetin, kaempferol, quercetin, lutein, and omega-3-phosphilipid complex. In certain embodiments, the dietary supplement comprises a derivative of one or more component.

In certain embodiments, a dietary supplement comprises about 2 mg/day to about 100 mg/day of riboflavin 5' phosphate, about 25 mg/day to about 250 mg/day of nicotinamide, about 10 μg/day to about 1000 μg/day of methylcobalamin, about 20 μg/day to about 100 μg/day of cholecalciferol, about 50 μg/day to about 5000 μg/day of phylloquinone, about 15 mg/day to about 250 mg/day of alpha-tocopherol, about 15 mg/day to about 1250 mg/day of gamma-tocopherol, about 1 mg/day to about 10 mg/day of benfotiamine, about 25 mg/day to about 400 mg/day of magnesium, about 1 mg/day to about 100 mg/day of myricetin, about 2 mg/day to about 200 mg/day of kaempferol, about 10 mg/day to about 400 mg/day of quercetin, about 2 mg/day to about 50 mg/day of lutein, and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 20 mg/day of riboflavin 5' phosphate, about 50 mg/day of nicotinamide, about 1000 μg/day of methylcobalamin, about 35 μg/day of cholecalciferol, about 250 μg/day of phylloquinone, about 20 mg/day of alpha-tocopherol, about 40 mg/day of gamma-tocopherol, about 5 mg/day of benfotiamine, about 70 mg/day of magnesium, about 10 mg/day of myricetin, about 30 mg/day of kaempferol, about 100 mg/day of quercetin, about 5 mg/day of lutein, and an omega-3-phospholipid complex including DHA in an amount of about 400 mg/day and EPA in an amount of about 200 mg/day. In certain embodiments, the dietary supplement comprises a derivative of one or more component.

In certain embodiments, a dietary supplement comprises riboflavin 5' phosphate, nicotinamide, methylcobalamin, cholecalciferol, phylloquinone, alpha-tocopherol, gamma-tocopherol, benfotiamine, magnesium, myricetin, kaempferol, quercetin, isorhamnetin, pelargonidin, malvidin, lutein, catechin composition, and omega-3-phospholipid complex.

In certain embodiments, the dietary supplement comprises a derivative of one or more component.

In certain embodiments, a dietary supplement comprises about 2 mg/day to about 100 mg/day of riboflavin 5' phosphate, about 25 mg/day to about 250 mg/day of nicotinamide, about 10 μg/day to about 1000 μg/day of methylcobalamin, about 20 μg/day to about 100 μg/day of cholecalciferol, about 50 μg/day to about 5000 μg/day of phylloquinone, about 15 mg/day to about 250 mg/day of alpha-tocopherol, about 15 mg/day to about 1250 mg/day of gamma-tocopherol, about 1 mg/day to about 10 mg/day of benfotiamine, about 25 mg/day to about 400 mg/day of magnesium, about 1 mg/day to about 100 mg/day of myricetin, about 2 mg/day to about 200 mg/day of kaempferol, about 10 mg/day to about 400 mg/day of quercetin, about 1 mg/day to about 100 mg/day of isorhamnetin, about 2 mg/day to about 150 mg/day of pelargonidin, about 10 mg/day to about 400 mg/day of malvidin, about 2 mg/day to about 50 mg/day of lutein, about 40 mg/day to about 1500 mg/day of a catechin composition (comprising about 30 mg/day to about 500 mg/day of EGCG with the remainder of the catechin composition being comprised of EGC, ECG, and/or EC), and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 20 mg/day of riboflavin 5' phosphate, about 50 mg/day of nicotinamide, about 1000 μg/day of methylcobalamin, about 35 μg/day of cholecalciferol, about 250 μg/day of phylloquinone, about 20 mg/day of alpha-tocopherol, about 40 mg/day of gamma-tocopherol, about 5 mg/day of benfotiamine, about 70 mg/day of magnesium, about 10 mg/day of myricetin, about 30 mg/day of kaempferol, about 100 mg/day of quercetin, about 5 mg/day of isorhamnetin, about 15 mg/day of pelargonidin, about 60 mg/day of malvidin, about 5 mg/day of lutein, about 240 mg/day of a catechin composition (comprising about 160 mg/day of EGCG with the remainder of the catechin composition being comprised of EGC, ECG, and/or EC), and an omega-3-phospholipid complex including DHA in an amount of about 400 mg/day and EPA in an amount of about 200 mg/day. In certain embodiments, the dietary supplement comprises a derivative of one or more component.

In certain embodiments, a dietary supplement comprises nicotinamide, pyridoxine, 5-methyltetrahydrofolate, hydroxocobalamin, cholecalciferol, alpha-tocopherol, gamma-tocopherol, phylloquinone, magnesium, quercetin, myricetin, kaempferol, isorhamnetin, lutein (including zeaxanthin), pelargonidin, malvidin, cyanidin, pterostilbene, catechin composition, l-theanine, and omega-3-phospholipid complex. In certain embodiments, the dietary supplement comprises a derivative of one or more component.

In certain embodiments, a dietary supplement comprises about 25 mg/day to about 250 mg/day of nicotinamide, about 1 mg/day to about 50 mg/day of pyridoxine, about 100 μg/day to about 1000 μg/day of 5-methyltetrahydrofolate, about 10 μg/day to about 1000 μg/day of hydroxocobalamin, about 20 μg/day to about 100 μg/day of cholecalciferol, about 15 mg/day to about 250 mg/day of alpha-tocopherol, about 15 mg/day to about 1250 mg/day of gamma-tocopherol, about 50 μg/day to about 5000 μg/day of phylloquinone, about 25 mg/day to about 400 mg/day of magnesium, about 10 mg/day to about 400 mg/day of quercetin, about 1 mg/day to about 100 mg/day of myricetin, about 2 mg/day to about 200 mg/day of kaempferol, about 1 mg/day to about 100 mg/day of isorhamnetin, about 2 mg/day to about 50 mg/day of lutein (including zeaxanthin), about 2 mg/day to about 150 mg/day of pelargonidin, about 10 mg/day to about 400 mg/day of malvidin, about 15 mg/day to about 500 mg/day of cyanidin, about 0.010 mg/day to about 5 mg/day of pterostilbene, about 40 mg/day to about 1500 mg/day of a catechin composition (comprising about 30 mg/day to about 500 mg/day of EGCG with the remainder of the catechin composition being comprised of EGC, ECG, and/or EC), about 5 mg/day to about 750 mg/day of l-theanine, and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 50 mg/day of nicotinamide, about 5 mg/day of pyridoxine, about 400 μg/day of 5-methyltetrahydrofolate, about 20 μg/day of hydroxocobalamin, about 30 μg/day of cholecalciferol, about 20 mg/day of alpha-tocopherol, about 40 mg/day of gamma-tocopherol, about 250 μg/day of phylloquinone, about 50 mg/day of magnesium, about 100 mg/day of quercetin, about 10 mg/day of myricetin, about 30 mg/day of kaempferol, about 5 mg/day of isorhamnetin, about 6 mg/day of lutein (including zeaxanthin), about 5 mg/day of pelargonidin, about 10 mg/day of malvidin, about 15 mg/day of cyanidin, about 0.025 mg/day of pterostilbene, about 160 mg/day of a catechin composition (comprising about 100 mg/day of EGCG with the remainder of the catechin composition being comprised of EGC, ECG, and/or EC), about 50 mg/day of l-theanine, and an omega-3-phospholipid complex including DHA in an amount of about 200 mg/day and EPA in an amount of about 60 mg/day. In certain embodiments, the dietary supplement comprises a derivative of one or more component.

In certain embodiments, a dietary supplement comprises nicotinamide, pyridoxine, 5-methyltetrahydrofolate, hydroxocobalamin, cholecalciferol, alpha-tocopherol, gamma-tocopherol, phylloquinone, magnesium, quercetin, myricetin, kaempferol, lutein (including zeaxanthin), pelargonidin, malvidin, cyanidin, pterostilbene, catechin composition, l-theanine, and omega-3-phospholipid complex. In certain embodiments, the dietary supplement comprises a derivative of one or more component.

In certain embodiments, a dietary supplement comprises about 25 mg/day to about 250 mg/day of nicotinamide, about 1 mg/day to about 50 mg/day of pyridoxine, about 100 μg/day to about 1000 μg/day of 5-methyltetrahydrofolate, about 10 μg/day to about 1000 μg/day of hydroxocobalamin, about 20 μg/day to about 100 μg/day of cholecalciferol, about 15 mg/day to about 250 mg/day of alpha-tocopherol, about 15 mg/day to about 1250 mg/day of gamma-tocopherol, about 50 μg/day to about 5000 μg/day of phylloquinone, about 25 mg/day to about 400 mg/day of magnesium, about 10 mg/day to about 400 mg/day of quercetin, about 1 mg/day to about 100 mg/day of myricetin, about 2 mg/day to about 200 mg/day of kaempferol, about 2 mg/day to about 50 mg/day of lutein (including zeaxanthin), about 2 mg/day to about 150 mg/day of pelargonidin, about 10 mg/day to about 400 mg/day of malvidin, about 15 mg/day to about 500 mg/day of cyanidin, about 0.010 mg/day to about 5 mg/day of pterostilbene, about 40 mg/day to about 1500 mg/day of a catechin composition (comprising about 30 mg/day to about 500 mg/day of EGCG with the remainder of the catechin composition being comprised of EGC, ECG, and/or EC), about 5 mg/day to about 750 mg/day of l-theanine, and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 50 mg/day of nicotinamide, about 5 mg/day of pyridoxine, about 400 μg/day of 5-methyltetrahydrofolate, about 20 μg/day of hydroxocobalamin, about 30 μg/day of cholecalciferol, about 20 mg/day of alpha-tocopherol, about 40 mg/day of gamma-tocopherol, about 250 μg/day of phylloquinone, about 50 mg/day of magnesium, about 100 mg/day of quercetin, about 10 mg/day of myricetin, about 30 mg/day of kaempferol, about 6 mg/day of lutein (including zeaxanthin), about 10 mg/day of pelargonidin, about 25 mg/day of malvidin, about 50 mg/day of cyanidin, about 0.025 mg/day of pterostilbene, about 320 mg/day of a catechin composition (comprising about 200 mg/day of EGCG with the remainder of the catechin composition being comprised of EGC, ECG, and/or EC), about 50 mg/day of l-theanine, and an omega-3-phospholipid complex including DHA in an amount of about 200 mg/day and EPA in an amount of about 60 mg/day. In certain embodiments, the dietary supplement comprises a derivative of one or more component.

In certain embodiments, a dietary supplement comprises nicotinamide, hydroxocobalamin, cholecalciferol, alpha-tocopherol, gamma-tocopherol, magnesium, quercetin, myricetin, kaempferol, lutein (including zeaxanthin), malvidin, cyanidin, pterostilbene, catechin composition, l-theanine, and omega-3-phospholipid complex. In certain embodiments, the dietary supplement comprises a derivative of one or more component.

In certain embodiments, a dietary supplement comprises about 25 mg/day to about 250 mg/day of nicotinamide, about 10 μg/day to about 1000 μg/day of hydroxocobalamin, about 20 μg/day to about 100 μg/day of cholecalciferol, about 15 mg/day to about 250 mg/day of alpha-tocopherol, about 15 mg/day to about 1250 mg/day of gamma-tocopherol, about 25 mg/day to about 400 mg/day of magnesium, about 10 mg/day to about 400 mg/day of quercetin, about 1 mg/day to about 100 mg/day of myricetin, about 2 mg/day to about 200 mg/day of kaempferol, about 2 mg/day to about 50 mg/day of lutein (including zeaxanthin), about 10 mg/day to about 400 mg/day of malvidin, about 15 mg/day to about 5 mg/day of cyanidin, about 0.010 mg/day to about 5 mg/day of pterostilbene, about 40 mg/day to about 1500 mg/day of a catechin composition (comprising about 30 mg/day to about 500 mg/day of EGCG with the remainder of the catechin composition being comprised of EGC, ECG, and/or EC), about 5 mg/day to about 750 mg/day of l-theanine, and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 50 mg/day of nicotinamide, about 20 μg/day of hydroxocobalamin, about 30 μg/day of cholecalciferol, about 20 mg/day of alpha-tocopherol, about 40 mg/day of gamma-tocopherol, about 50 mg/day of magnesium, about 50 mg/day of quercetin, about 10 mg/day of myricetin, about 20 mg/day of kaempferol, about 6 mg/day of lutein (including zeaxanthin), about 10 mg/day of malvidin, about 15 mg/day of cyanidin, about 0.025 mg/day of pterostilbene, about 160 mg/day of a catechin composition (comprising about 100 mg/day of EGCG with the remainder of the catechin composition being comprised of EGC, ECG, and/or EC), about 50 mg/day of l-theanine, and an omega-3- phospholipid complex including DHA in an amount of about 200 mg/day and EPA in an amount of about 60 mg/day. In certain embodiments, the dietary supplement comprises a derivative of one or more component.

In certain embodiments, a dietary supplement comprises nicotinamide, pyridoxine, 5-methyltetrahydrofolate, hydroxocobalamin, an ascorbate, cholecalciferol, alpha-tocopherol, gamma-tocopherol, phylloquinone, magnesium, quercetin, myricetin, kaempferol, isorhamnetin, lutein (including zeaxanthin), pelargonidin, malvidin, cyanidin, pterostilbene, catechin composition, l-theanine, and omega-3-phospholipid complex. In certain embodiments, the dietary supplement comprises a derivative of one or more component.

In certain embodiments, a dietary supplement comprises about 25 mg/day to about 250 mg/day of nicotinamide, about 1 mg/day to about 50 mg/day of pyridoxine, about 100 μg/day to about 1000 μg/day of 5-methyltetrahydrofolate, about 10 μg/day to about 1000 μg/day of hydroxocobalamin, 30 mg/day to about 400 mg/day of an ascorbate, about 20 μg/day to about 100 μg/day of cholecalciferol, about 15 mg/day to about 250 mg/day of alpha-tocopherol, about 15 mg/day to about 1250 mg/day of gamma-tocopherol, about 50 μg/day to about 5000 μg/day of phylloquinone, about 25 mg/day to about 400 mg/day of magnesium, about 10 mg/day to about 400 mg/day of quercetin, about 1 mg/day to about 100 mg/day of myricetin, about 2 mg/day to about 200 mg/day of kaempferol, about 1 mg/day to about 100 mg/day of isorhamnetin, about 2 mg/day to about 50 mg/day of lutein (including zeaxanthin), about 2 mg/day to about 150 mg/day of pelargonidin, about 10 mg/day to about 400 mg/day of malvidin, about 15 mg/day to about 500 mg/day of cyanidin, about 0.010 mg/day to about 5 mg/day of pterostilbene, about 40 mg/day to about 1500 mg/day of a catechin composition (comprising about 30 mg/day to about 500 mg/day of EGCG with the remainder of the catechin composition being comprised of EGC, ECG, and/or EC), about 5 mg/day to about 750 mg/day of l-theanine, and an omega-3-phospholipid complex including DHA in an amount of about 70 mg/day to about 2000 mg/day and EPA in an amount of about 18 mg/day to about 2000 mg/day. In certain embodiments, the dietary supplement comprises a derivative of one or more component.

In certain embodiments, a dietary supplement comprises about 50 mg/day of nicotinamide, about 5 mg/day of pyridoxine, about 400 μg/day of 5-methyltetrahydrofolate, about 20 μg/day of hydroxocobalamin, about 60 mg/day of an ascorbate, about 30 μg/day of cholecalciferol, about 30 mg/day of alpha-tocopherol, about 60 mg/day of gamma-tocopherol, about 500 μg/day of phylloquinone, about 50 mg/day of magnesium, about 100 mg/day of quercetin, about 20 mg/day of myricetin, about 40 mg/day of kaempferol, about 5 mg/day of isorhamnetin, about 12 mg/day of lutein (including zeaxanthin), about 5 mg/day of pelargonidin, about 20 mg/day of malvidin, about 30 mg/day of cyanidin, about 0.100 mg/day of pterostilbene, about 160 mg/day of a catechin composition (comprising about 100 mg/day of EGCG with the remainder of the catechin composition being comprised of EGC, ECG, and/or EC), about 50 mg/day of l-theanine, and an omega-3-phospholipid complex including DHA in an amount of about 400 mg/day and EPA in an amount of about 200 mg/day. In certain embodiments, the dietary supplement comprises a derivative of one or more component.

In certain embodiments, the dietary supplement further comprises additional nutrients.

In certain embodiments, the dietary supplement further comprises a component to improve bioavailability. In certain embodiments, the component to improve bioavailability is selected from the group consisting of a food complex, whole food matrix, delayed or controlled release technology, multi-compartment capsules or capsule-in-capsule technology, phytosome or liposome technology, amino acid functionalization or chelation functionalization, partition or division of oil-soluble components from the remaining components (e.g. oil-soluble components in a softgel(s) and remaining components in a two-piece capsule(s)), cyclodextrin or other encapsulation technologies.

In certain embodiments, the dietary supplement is formulated as a once a day composition, a twice a day composition, a three times a day composition, an every other day composition, a once a week composition, a bi-weekly composition, or a monthly composition.

In certain embodiments, the dietary supplement is formulated as a dosage form selected from the group consisting of pill, tablet, caplet, soft gelatin or vegetarian capsule, hard gelatin or vegetarian capsule, lozenge, sachet, cachet, vegicap, liquid drop, liquid, gel, slurry, elixers, suspensions, emulsions, solutions, dragee, syrups, concentrated food product (for example, supplement bar), and tea bags.

In certain embodiments, the dietary supplement is a liquid, lyophilized, or otherwise dried. In certain embodiments, the dietary supplement includes diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol, complexation with metal ions, or incorporation of the material into or onto particulate preparations of polymeric compounds such as polylactic acid, polyglycolic acid, or hydrogels, or onto liposomes, microemulsions, micelles, lamellar or multilamellar vesicles, erythrocyte ghosts or spheroplasts. Such compositions will influence the physical state, solubility, stability, rate of in vivo release, and rate of in vivo clearance. Controlled or sustained release compositions include formulations in lipophilic depots (e.g., fatty acids, waxes, oils).

The dietary supplements described herein are for oral administration and can be formulated readily by combining the components with acceptable carriers well known in the art. Dietary supplements for oral administration can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Dietary supplements may also be formulated as push-fit capsules made of gelatin or sealed capsules made of gelatin and a plasticizer, such as glycerol or sorbitol. The push-fit capsules can contain the active ingredients in an admixture with a filler such as lactose, binders, starches, lubricants, talc, magnesium stearate or stabilizers. In soft capsules, the active compounds can be dissolved or suspended in suitable liquids, such as fatty oils, liquid paraffin, or liquid polyethylene glycols. In addition, stabilizers can be added.

In certain embodiments, the dietary supplement is formulated to deliver the daily dose in a single formulation. In certain embodiments, the dietary supplement is formulated to partition the daily dose of nutrients into separate dosage units (for example, some nutrients are contained in one capsule, while the remaining nutrients are contained in a second capsule). In certain embodiments, the dietary supplement is formulated to deliver a fraction of the daily dose and will be administered two or more times per day. In certain embodiments, the dietary supplement is formulated to deliver a dose equal to about half of a daily dose and will be administered twice per day. In some embodiments, the dose is administered every about 12 hours.

Methods

The dietary supplements administered in the following methods are as described herein.

Embodiments are directed to methods of maintaining or improving brain health in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting of pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of reducing the risk of neurodegenerative disease (such as Alzheimer's disease and Parkinson's disease) in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of slowing or protecting against the development of neurodegenerative disease or such disease pathology in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of ameliorating certain micronutrient intake inadequacies associated with maintenance of brain health, cognitive decline, risk of neurodegenerative disease, or neurodegenerative pathology in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of reducing risk or rate of cognitive decline, which may be age-related or otherwise, in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of providing intakes of certain nutrients so as to mimic (or complement) neuroprotective dietary patterns (e.g. MeDi, MIND, DASH, a posteriori patterns, or composites thereof) in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of maintaining or improving a mental or cognitive quality in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of maintaining or improving cerebrovascular health in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of maintaining or improving brain trophic factors (e.g. brain-derived neurotrophic factor) in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of maintaining or improving gut health, as it relates to brain health, in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of protecting from or treating toxin or toxic exposures, as it relates to brain health, in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of treating neurodegenerative disease in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of improving or maintaining health in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

Embodiments are directed to methods of maintaining certain areas of health, such as immune health, eye health, cardiovascular health, metabolic health, and longevity in a subject comprising administering to the subject a dietary supplement, wherein the dietary supplement comprises a water-soluble vitamin component, an oil-soluble vitamin component, magnesium or derivatives thereof, a primary polyphenolic compound, a secondary polyphenolic compound, and an omega-3-phospholipid complex; wherein the water-soluble vitamin component is selected from the group consisting of vitamin B1, vitamin B2, vitamin B3, vitamin B6, vitamin B9, vitamin B12, vitamin C, and combinations thereof; wherein the oil-soluble vitamin component is selected from the group consisting of vitamin D, vitamin K, vitamin E, vitamin B1, and combinations thereof; wherein the primary polyphenolic compound is selected from the group consisting of myricetin or derivative thereof, kaempferol or derivative thereof, quercetin or derivative thereof, isorhamnetin or derivative thereof, and combinations thereof; wherein the secondary polyphenolic compound is selected from the group consisting pelargonidin or derivative thereof, malvidin or derivative thereof, cyanidin or derivative thereof, delphinidin or derivative thereof, lutein or derivative thereof, resveratrol or derivative thereof, pterostilbene or derivative thereof, a catechin composition, and combinations thereof; and wherein the omega-3-phospholipid complex is selected from the group consisting of phospholipid forms of DHA, EPA, and combinations thereof.

In certain embodiments, brain health refers to cognitive ability and memory. Cognitive ability may be measured via standardized cognitive assessments, such as episodic memory, semantic memory, working memory, perceptual speed, and visuospatial ability tests. In certain embodiments, brain health refers to the mobility and sensory ability as mediated by the brain.

In certain embodiments, maintaining or improving brain health refers to the reduction of dietary deficiencies or consumption (intake) inadequacies, mitigating age-related changes in nutrient consumption, replacing dietary consumption levels that are not met as individuals age, or replacing dietary consumption levels of micronutrients associated with brain health.

In certain embodiments, the mental or cognitive quality is selected from the group consisting of age related cognitive or memory decline, normal brain function, cognitive ability, concentration, mental acuity, mental alertness, cognitive well-being, mental performance, memory, mental sharpness, mental vitality, mental clarity, short-term memory, learning, good brain health, and combinations thereof. Cognitive qualities may be measured via standardized cognitive assessments, such as episodic memory, semantic memory, working memory, perceptual speed, and visuospatial ability tests.

In certain embodiments, the cognitive decline may be a result of neuroinflammation, oxidative stress, gut dysbiosis, deficiencies in trophic factors, cerebrovascular damage, increased toxin accumulation, or mitochondrial dysfunction. Accordingly, administering the dietary supplement described herein may reduce neuroinflammation, reduce oxidative stress, mitigate intestinal microbiome alterations, mitigate deficiencies in trophic factors, improve cerebrovascular systems, improve toxin processing and excretion, or improve mitochondrial dysfunction.

In certain embodiments, cognitive decline refers to the deterioration of cognitive function, which includes a mental process that enables the gathering and processing of information, such as learning, thinking, reasoning, remembering, problem solving, decision making, and attention. Numerous tests have been developed to measure different aspects of cognitive function, examples of such tests include episodic memory, semantic memory, working memory, perceptual speed, and visuospatial ability tests.

In certain embodiments, the neurodegenerative disease is selected from diseases where neurons in the brain or peripheral nervous system progressively lose function and die, Alzheimer's disease, Parkinson's disease, Lewy body dementia (LBD), amyotrophic lateral sclerosis (ALS), Huntington's disease, or the effects of traumatic brain injury (TBI).

In certain embodiments, the neurodegenerative pathology is a characteristic structural or functional feature of a neurodegenerative disease as evidenced in blood or tissue specimens. In certain embodiments, the structural or functional feature is an abnormal deposition or aggregation of proteins, selected from amyloid beta, tau, and alpha synuclein.

In certain embodiments, the subject is at any stage of Alzheimer's disease, is in the pre-symptomatic or prodromal stage of Alzheimer's disease, is from early to mid-stage Alzheimer's disease, or is from mid to late stages of Alzheimer's disease.

In certain embodiments, the subject is at any stage of Parkinson's disease, is in the pre-symptomatic or prodromal stage of Parkinson's disease, is from early to mid-stage Parkinson's disease, or is from mid to late stages of Parkinson's disease.

In certain embodiments, the subject is older than 25 years old, 30 years old, 35 years old, 40 years old, 45 years old, 50 years old, 55 years old, 60 years old, 65 years old, 70 years old, 75 years old, 80 years old, 85 years old, 90 years old, or 95 years old.

In certain embodiments, the subject is healthy.

In certain embodiments, the subject has one or more risk factors for neurodegeneration or neurodegenerative disease. The risk factors are selected from the group consisting of age, sex, education, health history, family health history, sleep patterns, low mental activity, low social activity, certain genetic polymorphisms, poor nutrition, decreased physical activity, obesity, endocrine conditions, oxidative stress, inflammation, stroke, hypertension, diabetes, smoking, head trauma, depression, infection, tumors, vitamin or mineral or phytochemical deficiencies, immune and metabolic conditions, chemical exposure, occupation, geographic location, and combinations thereof.

Methods for Systematically Designing a Dietary Supplement

Embodiments described herein are directed to methods, including algorithms, for systematically determining a dietary supplement comprising: (i) selection of dietary patterns, including those whose adherence is related to brain health, neurodegenerative disease incidence, neurodegenerative disease pathogenesis, pathology or progression, and/or cognitive decline that is typically associated with aging, (ii) selection and/or definition of dietary components from such dietary patterns, (iii) transformation of dietary components into constituent nutrients, (iv) primary screening of constituent nutrients against human epidemiological evidence that relates such nutrients to outcomes in brain health, neurodegenerative disease incidence, neurodegenerative disease pathogenesis, pathology or progression, and/or cognitive decline that is typically associated with aging, (v) identifying nutrients for which there exist dietary inadequacies based on reference intakes, guidelines and/or changes in age-related requirements, (vi) confirmation of mechanism(s) of action (MOAs) by nutrients of interest that are relevant to the biological hallmarks of neurodegenerative diseases or aging of the brain, (vii) evaluation of the expected benefits and safety of nutrients of interest. Such method would yield a score, weighting, or rating for each nutrient of interest to support its inclusion or exclusion in formulations and recommended combination of such nutrients.

The methods that follow can be utilized to develop effective dietary supplement compositions for a variety of conditions or diseases, or to maintain health, such as immune health, eye health, cardiovascular health, metabolic health, and longevity. The methods described herein can be utilized to develop personalized dietary supplement compositions based upon a subject's age, sex, genetics, risk factors, diet, and/or level of exercise.

The methods described herein are novel due in-part to the following: (i) the selection and analysis of dietary patterns as the starting point for such methods, (ii) use of epidemiological evidence as the primary screen for nutrient candidates, (iii) establishment of a "rational design," systems-based methodology (akin to "rational design" methodologies applied to drug design, software development, and engineering) to derive nutrient compositions, including those embodied herein, by employment of a unique and specific sequence of analytical layers, and (iv) the absence of known rational design methodologies taught in prior art for the design of dietary supplements for brain health and/or neurodegenerative diseases.

The novelty of the methods described herein may be understood by comparison of standard dietary supplement design processes versus the methods described herein. Standard design processes typically follow a reductionist approach, building-up from individual parts (or nutrients, in this case): (i) selection of a candidate nutrient(s) to study, which may be motivated by diverse rationale, and (ii) testing and assessment of nutrient(s) in a non-clinical model (usually in vitro or non-human model) or assessment of tests already performed. The final output of such methods is an estimation of the effectiveness of the specific nutrient(s), as tested specifically in the context of the non-clinical model. In contrast, the methods described herein follow a systems approach, starting from a whole system (e.g. dietary patterns) and breaking it down to the most relevant parts to solve the problem at-hand: (i) analysis of dietary patterns, starting as a rule at a higher level of abstraction, and (ii) transformation of dietary patterns to components and then to nutrients, screening by human epidemiology, and a specific sequence of analytical layers as described herein. The final output of such methods is a group or combination of nutrients associated with maintenance of brain health or reduced risk of adverse changes in brain health and/or neurodegenerative diseases.

As a more detailed description, in certain embodiments, the methods described herein begin by examining medically-endorsed dietary patterns that have been studied through epidemiological, observational, and/or clinical means in relation to a variety of health outcomes, including neurodegenerative diseases and cognitive decline. Examples of such dietary patterns, the adherence to which is related to neurodegenerative disease incidence and cognitive decline particularly with aging, are the Mediterranean diet, Dietary Approaches to Stop Hypertension (DASH) diet, and MIND diet. Such dietary patterns are selected as the starting point, as they are inherently multi-factorial and therefore comprehensively encompass a large range of nutritional factors that may affect health outcomes. This approach is unique from the standard practice of starting first with an individual ingredient (or nutrient or extract; or specific group of nutrients) and then developing hypotheses regarding their effect on health outcomes.

Next, in certain embodiments, dietary components from such dietary patterns, which are associated with reduced risk of developing neurodegenerative diseases and/or cognitive decline, are selected and/or defined. Dietary components are transformed into constituent nutrients, which are mapped from a library of nutrients. The compositional embodiments described herein result from the specific application of the method described herein to population health-level data, such as data collected from national-, regional-, state-, and/or community-level cohorts. Dietary components selected or defined for such analysis include (i) fish/fish derivatives, (ii) leafy green vegetables, (iii) berries, (iv) tea, (v) beans and legumes, (vi) nuts, seeds, and their derivatives, (vii) poultry, (viii) other vegetables and fruits, and (ix) wine. A library of nutrients for common foods included in such dietary components was evaluated by application of an algorithmic method to evaluate whether such nutrients meet the principal epidemiological screen, as well as to assess dietary inadequacies, confirm MOA(s), evaluate expected benefits, and evaluate safety.

In certain embodiments, the algorithm then identifies and selects those nutrients or, if necessary, groupings of nutrients for which adequate human epidemiological or observational evidence has been generated regarding outcomes in brain health, neurodegenerative disease incidence, neurodegenerative disease pathogenesis, pathology or progression, and/or cognitive decline that is typically associated with aging. Such a screening technique, based upon human epidemiological or observational data is unique, since traditional primary screens are typically driven by in vitro mechanism-of-action or non-human models. The core limitation of such traditional screening methods is that their outcomes have historically failed to translate to humans in the area of neurodegenerative disease and long-term brain health, exemplified by a failure rate of 99.6% for Alzheimer's disease drug candidates that transition from animal (or preclinical) studies to humans, as well as there being no new drug for Alzheimer's disease approved by FDA in the past 15 years. Accordingly, we apply a less traditional approach in this case, screening principally against epidemiological evidence. Screening against the results of controlled and/or prospective cohort epidemiological studies represent a rigorous approach, as such studies typically require substantial subject recruitment and follow-up efforts, multi-disciplinary research staff, and data collection and analysis infrastructure, which typically represents a greater investment than in vitro or non-human animal model studies. Importantly, epidemiological evidence is likely to be more relevant to human health, since the data is based upon human outcomes. In certain embodiments, the evaluation of each nutrient using human epidemiological evidence is performed in conjunction with a dosage screen to determine if the nutrient can be presented in a dietary supplement composition in a feasible (or practical) daily dose.

In certain embodiments, for the selected nutrients or grouping of nutrients, the algorithm then identifies those for which there is a dietary inadequacy. Dietary inadequacies are identified by comparison of nutrient intake levels with dietary reference intakes (DRIs), USDA dietary guidelines, changes in intake requirements as people age, and/or potential functional inadequacies that are unaccounted for in current DRIs or dietary guidelines. Nutrients for which a dietary inadequacy is identified are referred to as nutrients of interest.

In certain embodiments, the algorithm is then applied to confirm the scientific relevance of the nutrient towards one or more mechanistic (or biological) hallmarks of neurodegenerative disease pathogenesis and/or progression. Confirmation for each nutrient of interest is conducted through survey and analysis of mechanism of action (MOA) studies conducted through in vitro, in vivo or other relevant MOA models. The mechanistic hallmarks are classified as (i) oxidative stress, (ii) inflammation or irregular immune response, (iii) toxic or toxin exposure, (iv) mitochondrial or cellular energetics dysfunction, (v) irregularity in trophic factors, (vi) microbiome or gut dysfunction, and (vii) cerebrovascular factors related to the central and peripheral nervous system, and hallmarks may be added, removed, and/or consolidated as research provides further elucidation of such mechanisms.

Next, in certain embodiments, the algorithm is applied to evaluate the expected benefit of each nutrient of interest, which relies primarily upon the results of epidemiological studies and clinical studies for which each such nutrient is studied for its effect on outcomes with relevance to neurodegenerative disease incidence, prevention, treatment or disease modification or brain health outcomes, such as those for cognitive function or abilities. In addition, the algorithm is applied to evaluate the safety and/or safe dosage levels of each nutrient of interest, which utilizes toxicological study data, DRI upper tolerable limits, clinical study safety readouts, and/or epidemiological study outcomes to establish safety ratings and limits.

In certain embodiments, the algorithm described herein provides customization (precision nutrition) based on variation at the individual level or population subset level. Population-level data by its nature cannot account for all variation, or identify optimal treatments for individuals or population subsets within a broader population, as unique circumstances or backgrounds may require alterations to nutritional regimens to account for the ways an individual or population subset differs from the population mean. Such variation from the mean allows for additional optimization of dietary supplement dosages by accounting for such unique characteristics. This customization could incorporate multiple sources of information, including genetics, microbiome, age, employment, lifestyle, familial history, metabolic response to specific foods, co-morbidities and geographic location. These characteristics and information may be applied to determine how a formulation derived using population-level data and metrics would be modified to suit a unique individual or population subset.

In certain embodiments, precision nutrition is applied to the algorithm as described using the population-level data, affecting multiple levels of the algorithm as described: (i) customization can be performed according to a determination of dietary inadequacy; this dietary customization can be based on age, genetics, geographic location, microbiome and/or self-reported dietary habits; (ii) customization can be applied to the specific MOAs of specific nutrients that are linked to specific hallmarks of neurodegenerative disease, neurodegenerative disease pathology or cognitive decline; this customization can be informed by age, geographic location, metabolic responses, genetics, employment, and/or lifestyle factors; (iii) the customization can be applied to the weighted risk reduction and benefit determination; this customization can be informed by age, geographic location, metabolic responses, familial history, genetics, employment, and/or lifestyle factors. Customization includes the up- or down-weighting of certain factors or coefficients or introduction or removal of certain factors or coefficients, which would result in the inclusion, exclusion, increase or decrease of specific nutrients to suit an individual or population subset.

In certain embodiments, nutrients of interest qualify for consideration in a dietary supplement composition by meeting or exceeding a threshold composite score, which is comprised of sub-scores evaluating epidemiological evidence basis, dietary inadequacy, relevance of MOA(s), expected benefit, and safety or safe dosage levels. In certain embodiments, a nutrient may be limited in dosage level or disqualified from consideration based upon defined constraints regarding weight, volume, or composite score.

In certain embodiments, dietary components are identified based on quantitative measurements published by the United States Department of Agriculture (USDA) or other research institutions. In certain embodiments, dietary components are selected from fish/fish products, leafy green vegetables, botanical fruits including dry fruits (examples including fruits such as, legumes, beans, nuts, seeds, achene, fibrous drupes, cypsela), fleshy fruits (examples including pepo, hesperidium, berries, multiple or aggregate fruits and stone fruits), teas, poultry, whole grains, plant rhizomes, wine or other culinary vegetables or fruits. In certain embodiments, the nutrient class is selected from the group consisting of vitamins, minerals, anthocyanidin, flavon-3-ols, theaflavins, flavones, flavonols, isoflavones, carotenoids, other phytochemicals, and fats. In certain embodiments, the micronutrients are selected from a nutrient library, including flavonoids tracked in the USDA Database for the Flavonoid Content of Selected Foods; phytochemicals, such as luteolin, apigenin, tangeritin, curcumin, cyanidin, delphinidin, malvidin, pelargonidin, peonidin, petunidin, quercetin, kaempferol, myricetin, fisetin, galangin, isorhamnetin, pachypodol, rhamnazin, pyranoflavonols, furanoflavonols, hesperetin, naringenin, eriodictyol, homoeriodictyol, catechin, gallocatechin, catechin 3-gallate, gallocatechin 3-gallate, epicatechins, epigallocatechin, epicatechin 3-gallate, epigallocatechin 3-gallate, gastrodin, baicalein, astaxanthin, and resveratrol; metals and minerals, such as selenium, zinc, copper, calcium, and magnesium; vitamins; fatty acids, such as DHA, EPA, arachidonic acid, linolenic acid, linoleic acid, palmitic acid, lipoic acid, certain other medium chain triglycerides, and certain other short-chain fatty acids; other nutritional small molecules and cofactors, such as ubiquinone, idebenone, nitrate, pyruvate, and pyrroloquinoline quinone; amino acids, phospholipids, and proteins, including creatine, acetyl-1-carnitine, phosphatidyl serine, n-acetyl cysteine, 1-glutamine, collagen, and glutathione; and other hormones or drugs, such as estrogen, genistein, melatonin, and caffeine.

In certain embodiments, mathematically, each dietary component can be represented as the summation of the all the micronutrients, where each nutrient class has a unique vector of constants, K, that has been determined for that nutrient class. This is represented by Formula I.

$$f(\text{dietary component}) = \\ \sum_a^i \begin{pmatrix} K_{a1} \\ K_{a2} \\ \dots \\ K_{an} \end{pmatrix} (a_1 + a_2 \dots) + \begin{pmatrix} K_{b1} \\ K_{b2} \\ \dots \\ K_{bn} \end{pmatrix} (b_1 + b_1 \dots) + \dots \qquad \text{Formula I}$$

In certain embodiments, a score is calculated using a matrix transformation utilizing a 5 layer analysis. The matrix transformation is applied to identify micronutrients that are most representative of a dietary component. In certain embodiments, the matrix transformation, as represented by Formula II, which is a product of layer 1 and a summation of layers 2, 3, and 4. Layers 2 through 4 are weighted calculations to determine the strength of evidence for a micronutrient. The total evidence weighting for a micronutrient is the summation of layers 2-4, and the multiplication with layer 1 (which is a Boolean operation) which results in the entire summation to remain unchanged, or sets the dosage to zero.

$$f_{i1\_4}(\text{nutrient})=f_1(\text{nutrient})*\Sigma_{i=2}^4 f_i(\text{nutrient}) \qquad \text{Formula II}$$

In certain embodiments, layer 1 is a Boolean operation which determines whether to proceed with the micronutrient analysis. For a given micronutrient, analysis only continues if either criteria of having a longitudinal, or cross-sectional human epidemiological study out of which brain health outcomes may be derived, as represented by Formula III. Studies may be scored based on quality of study design or performance, and excluded as a result of this metric.

$$f_{i1}(\text{micronutrient})=(\text{Longitudinal Epi Study})\bigvee(\text{Cross-} \\ \text{sectional Epi Study}) \qquad \text{Formula III}$$

In certain embodiments, layer 2 is a determination of the dietary inadequacy for a micronutrient. This is a weighted calculation that determines the importance of a micronutrient based on inadequacy within the population or an individual. The total output of layer 2 is determined by Formula IV.

$$f_{i2}(\text{micronutrient}) = K_1 * \left[ 1 - \frac{(e(x, \text{ age}) - c(x, \text{ age}))}{c(x, \text{ age})} \right] \qquad \text{Formula IV}$$

where c(x) is an ideal consumption for a given micronutrient at a given age:

$$c(x, \text{ age}) = \begin{cases} US\ RDI, & \text{if } RDI \text{ exists} \\ f(USDA \text{ Dietary guidlines}), & \text{if no } RDI \end{cases}$$

where f (USDA Dietary guidlines) is constructed from USDA recommended consumption of foods, or food groups and using those recommended quantities to calculate an exemplary consumption level for each micronutrient, where e(x) is the expected consumption for a micronutrient, food or food group as a function of age is derived from epidemiological evidence:

$$e(x,\text{age})=f(\text{Epidemiological Evidence}),$$

where $K_1$ is a term that may be used for weighting and is determined based on potential differences in processing or availability of a micronutrient. In certain embodiments, $K_1$ may be used to provide personalization for a specific individual given additional information such as genotype, family history, lifestyle factors, geographic location, proximity to sources of pollution, etc:

$$K_1=f(\text{genotype,microbiome,etc}).$$

In certain embodiments, layer 3 is a determination of the evidentiary strength for a given micronutrient given the known mechanisms of action (MOA) for a micronutrient, and the importance of the MOA to specific known hallmarks of neurodegenerative disease. Hallmarks are defined as common denominators and physiological or biological changes that are shared between multiple neurodegenerative diseases or cognitive decline. These hallmarks include gut microbiome dysbiosis, altered inflammatory responses (including increased neuroinflammation), exposure to environmental toxins, metabolic syndrome or altered glucose metabolism, protein misfolding and plaque accumulation, mitochondrial dysfunction and altered cellular energetics, increased oxidative stress, and reduced neurotrophic factors. This is a weighted calculation that determines the importance of a micronutrient to this layer, as represented by Formula V.

$$f_{i3}(\text{micronutrient}) = f_{H1}(\text{micronutrient}) + f_{H2}(\text{micronutrient}) \ldots + f_{Hn}(\text{micronutrient}) \quad \text{Formula V}$$

where $f_H$ are biochemical and physiological hallmarks of neurodegeneration. Examples are gut microbiome dysbiosis, altered inflammatory responses (including increased neuroinflammation), exposure to environmental toxins, metabolic syndrome or altered glucose metabolism, protein misfolding and plaque accumulation, mitochondrial dysfunction and altered cellular energetics, increased oxidative stress, and reduced neurotrophic factors $$f_{H1} = K_{H1} * \Sigma_{i=1}{}^n P(\text{Harm Reduction}|\text{Micronutrient MOA}_i)$$

where $K_{H1}$ is weighting constant that incorporates the strength and importance of the hallmark to the progression of the disease. This may be used to provide personalization for a specific individual given additional information such as genotype, family history, lifestyle factors, etc.

$$K_{H1} = f(\text{Hallmark Importance}|\text{genotype,microbiome, etc})$$

where $P(\text{Harm Reduction}|\text{Micronutrient MOA}_i)$ is an output given the number, quality and type of experiments used to determine the micronutrient MOA. This may be determined based on the appropriateness for a disease state. For example, nutrient MOAs that have been studied using multiple animal models would increase confidence more than a single study performed using cell culture.

In certain embodiments, layer 4 is a determination of the evidentiary strength for a given micronutrient or dietary component given human clinical evidence (random controlled trials—RCT) and human epidemiological data. This is a weighted calculation that averages the clinical and epidemiological evidence represented by Formula VI.

$$f_{i4}(\text{micronutrient}) = \frac{f_{CE}(\text{micro nutrient}) + f_{EPI}(\text{micronutrient})}{2} \quad \text{Formula VI}$$

$$\text{where } f_{CE}(\text{micronutrient}) = \frac{\sum_{i}^{n} K_{CE\_i} * \dfrac{Dosage_i}{c(\text{micronutrient})}}{\sum_{i}^{n} K_{CE\_i}},$$

where $K_{CE\_i}$ is a weighting constant that incorporates the quality of the experimental design, and the reported outcome (Dosages used in clinical experiments both with higher quality, and better outcomes receive higher weights), where c(micronutrient) is the ideal consumption for a given micronutrient or dietary component at a given age as given in the description of layer 2, where $$f_{EPI}(\text{micronutrient}) = \frac{\sum_{i}^{n} K_{EPI\_i} * \dfrac{TC_i}{c(\text{nutrient})}}{\sum_{i}^{n} K_{EP\_i}},$$

where $K_{EPI\_i}$ is a weighting constant that incorporates that quality of the experimental design, and the reported outcome (Epidemiological experiments both with higher quality design and data, and better outcomes receive higher weights), where $TC_i$ is the mean consumption for the given micronutrient in the highest group studied (quartile, quintile, etc), where c(micronutrient) is the ideal consumption for a micronutrient or dietary component at a given age as given in the description of layer 2.

In certain embodiments, layer 5 is a safety and tolerability limit imposed on the dosage level. This incorporates information about safety and toxicity clinical studies, as well as the upper limit suggested by the DRI (if available). Critically, the weightings at layers 2-4 are designed so that the final output is within the range of 0-5. And this weighting is then used to determine final recommended dosage, as represented by Formula VII.

$$r(\text{micronutrient}) = f_{safety}(f_{i1-4}(\text{micronutrient}) * c(\text{micronutrient}), \text{micronutrient}) \quad \text{Formula VII}$$

where the recommended dosage for a micronutrient is the weighted output of layers 1-4 as detailed above, multiplied by c(x) which the ideal consumption for a micronutrient or dietary component at a given age as given in the description of layer 2.

The safety function determines the upper limit of dosage and ensures that the recommended dosage falls below that. This is calculated by taking the minimum of desired dosage, and two upper limits, as represented by Formula VIII.

$$f_{safety}(x, \text{nutrient}) = \min(x, K_{DRI} * UL_{RDI}(\text{nutrient}), K_{TOX} * UL_{TOX}(\text{nutrient})) \quad \text{Formula VIII}$$

where $UL_{DRI}$ is determined using the DRI upper limit, if it exists, for the specific nutrient and where the domain of the safety factor $K_{DRI}$ is [0, 1). Similarly, $UL_{TOX}$ is determined as an upper limit from clinical toxicological and tolerability research and where the domain of the safety factor $K_{TOX}$ is [0, 1).

This invention and embodiments illustrating the method and materials used may be further understood by reference to the following non-limiting examples. Although the present invention has been described in considerable detail with reference to certain preferred embodiments thereof, other versions are possible. Therefore, the spirit and scope of the appended claims should not be limited to the description and the preferred versions contained within this specification.

EXAMPLES

Example 1: Dietary Supplement Formulations

The following are examples of dietary supplement formulations according to the compositions as described herein, containing the following nutrients in at least the amounts indicated. The dietary supplement may be presented in capsule form, powder form or other forms as previously described.

Example Formulation 1

| Nutrient | Daily dose | Unit of measure |
|---|---|---|
| Water-soluble vitamin component | | |
| Vitamin B3 (nicotinamide) | 50 | mg |
| Vitamin B6 (pyridoxine) | 5 | mg |
| Vitamin B9 (5-methyltetrahydrofolate) | 0.400 | mg |
| Vitamin B12 (hydroxocobalamin) | 0.020 | mg |
| Oil-soluble vitamin component | | |
| Vitamin D3 (cholecalciferol) | 0.030 | mg |
| Vitamin E (d-alpha-tocopherol) | 20 | mg |
| Vitamin E (gamma-tocopherol) | 40 | mg |
| Vitamin K (phyloquinone) | 0.250 | mg |
| Magnesium or derivative component | | |
| Magnesium (elemental) | 50 | mg |
| Primary polyphenolic compound | | |
| Quercetin | 100 | mg |
| Myricetin | 10 | mg |
| Kaempferol | 30 | mg |
| Isorhamnetin | 5 | mg |
| Secondary polyphenolic compound | | |
| Lutein | 5 | mg |
| Zeaxanthin | 1 | mg |
| Pelargonidin | 5 | mg |
| Malvidin | 10 | mg |
| Cyanidin | 15 | mg |
| Pterostilbene | 0.025 | mg |
| Catechins | 160 | mg |
| L-theanine | 50 | mg |
| Omega-3-phospholipid complex | | |
| Docosahexaenoic acid (phospholipid form) | 200 | mg |
| Eicosapentaenoic acid (phospholipid form) | 60 | mg |

Example Formulation 2

| Nutrient | Daily dose | Unit of measure |
|---|---|---|
| Water-soluble vitamin component | | |
| Vitamin B3 (nicotinamide) | 50 | mg |
| Vitamin B6 (pyridoxine) | 5 | mg |
| Vitamin B9 (5-methyltetrahydrofolate) | 0.400 | mg |
| Vitamin B12 (hydroxocobalamin) | 0.020 | mg |
| Oil-soluble vitamin component | | |
| Vitamin D3 (cholecalciferol) | 0.030 | mg |
| Vitamin E (d-alpha-tocopherol) | 20 | mg |
| Vitamin E (gamma-tocopherol) | 40 | mg |
| Vitamin K (phylloquinone) | 0.250 | mg |
| Magnesium or derivative component | | |
| Magnesium (elemental) | 50 | mg |
| Primary polyphenolic compound | | |
| Quercetin | 100 | mg |
| Myricetin | 10 | mg |
| Kaempferol | 30 | mg |
| Secondary polyphenolic compound | | |
| Lutein | 5 | mg |
| Zeaxanthin | 1 | mg |
| Pelargonidin | 10 | mg |
| Malvidin | 25 | mg |
| Cyanidin | 50 | mg |
| Pterostilbene | 0.025 | mg |

-continued

| Nutrient | Daily dose | Unit of measure |
|---|---|---|
| Catechins | 320 | mg |
| L-theanine | 50 | mg |
| Omega-3-phospholipid complex | | |
| Docosahexaenoic acid (phospholipid form) | 200 | mg |
| Eicosapentaenoic acid (phospholipid form) | 60 | mg |

Example Formulation 3

| Nutrient | Daily dose | Unit of measure |
|---|---|---|
| Water-soluble vitamin component | | |
| Vitamin B3 (nicotinamide) | 50 | mg |
| Vitamin B12 (hydroxocobalamin) | 0.020 | mg |
| Oil-soluble vitamin component | | |
| Vitamin D3 (cholecalciferol) | 0.030 | mg |
| Vitamin E (d-alpha-tocopherol) | 20 | mg |
| Vitamin E (gamma-tocopherol) | 40 | mg |
| Magnesium or derivative component | | |
| Magnesium (elemental) | 50 | mg |
| Primary polyphenolic compound | | |
| Quercetin | 50 | mg |
| Myricetin | 10 | mg |
| Kaempferol | 20 | mg |
| Secondary polyphenolic compound | | |
| Lutein | 5 | mg |
| Zeaxanthin | 1 | mg |
| Malvidin | 10 | mg |
| Cyanidin | 15 | mg |
| Pterostilbene | 0.025 | mg |
| Catechins | 160 | mg |
| L-theanine | 50 | mg |
| Omega-3-phospholipid complex | | |
| Docosahexaenoic acid (phospholipid form) | 200 | mg |
| Eicosapentaenoic acid (phospholipid form) | 60 | mg |

Example Formulation 4

| Nutrient | Daily dose | Unit of measure |
|---|---|---|
| Water-soluble vitamin component | | |
| Vitamin B3 (nicotinamide) | 50 | mg |
| Vitamin B6 (pyridoxine) | 5 | mg |
| Vitamin B9 (5-methyltetrahydrofolate) | 0.400 | mg |
| Vitamin B12 (hydroxocobalamin) | 0.020 | mg |
| Vitamin C (ascorbate) | 60 | mg |
| Oil-soluble vitamin component | | |
| Vitamin D3 (cholecalciferol) | 0.030 | mg |
| Vitamin E (d-alpha-tocopherol) | 30 | mg |
| Vitamin E (gamma-tocopherol) | 60 | mg |
| Vitamin K (phyloquinone) | 0.500 | mg |
| Magnesium or derivative component | | |
| Magnesium (elemental) | 50 | mg |

-continued

| Nutrient | Daily dose | Unit of measure |
|---|---|---|
| Primary polyphenolic compound | | |
| Quercetin | 100 | mg |
| Myricetin | 20 | mg |
| Kaempferol | 40 | mg |
| Isorhamnetin | 5 | mg |
| Secondary polyphenolic compound | | |
| Lutein | 10 | mg |
| Zeaxanthin | 2 | mg |
| Pelargonidin | 5 | mg |
| Malvidin | 20 | mg |
| Cyanidin | 30 | mg |
| Pterostilbene | 0.100 | mg |
| Catechins | 160 | mg |
| L-theanine | 50 | mg |
| Omega-3-phospholipid complex | | |
| Docosahexaenoic acid (phospholipid form) | 400 | mg |
| Eicosapentaenoic acid (phospholipid form) | 200 | mg |

Example 2: Human Prospective Observational Studies of Embodied Nutrients

Objective: Nutrient combinations of one or more nutrients of interest for the described embodiments may be studied through human prospective observational studies to evaluate the effect of varying intake levels of such nutrients on the maintenance of brain health or risk of developing neurodegeneration, evaluating (i) rate of cognitive decline, (ii) incidence of neurodegenerative disease, and/or (iii) neurodegenerative disease pathology.

Study subjects and food frequency questionnaire: Study subjects (participants) would preferably be free of known neurodegenerative disease (for example, diagnosed Alzheimer's disease, Parkinson's disease or dementia) upon enrollment, agree to periodic evaluations, and/or agree to organ donation after death. For evaluations, study participants would be asked to complete food frequency questionnaires (FFQs), which would capture participants' intake from a list of food items. The intake of nutrients, particularly those of the nutrient combination of interest, would be computed using a database(s) that relates nutrient content to each specific food item. Study participants would be followed for a period of time, and their health outcomes would be recorded.

Assessment of cognitive decline: Each participant would undergo periodic evaluations that include a battery of cognitive tests. Cognitive tests could characterize cognition across a cognitive domains, such as episodic memory, working memory, semantic memory, visuospatial ability and/or perceptual speed. Each cognitive domain could be assessed through a tests, and composite scores could be derived from multiple test scores to provide domain- or global-level assessments. Scores could be normalized or standardized to facilitate analysis. Statistical methods or modeling would be used to relate specific nutrient(s) intake with the rate of change in cognitive scores. Other variables, which may include age, sex, education, and/or genetics, would be considered in statistical analysis to understand their effect or interaction with nutrient intakes.

Assessment of incident neurodegenerative disease: Each participant would undergo periodic evaluations to determine whether the participant should be clinically diagnosed with a neurodegenerative disease, such as Alzheimer's or Parkinson's disease. Diagnoses would be made by an experienced clinician or health care practitioner. Diagnoses would incorporate well-accepted diagnostic information, such as a neurological examination, medical history, and/or cognitive testing. Diagnoses would be based upon criteria promulgated by an appropriate medical, patient advocacy or governmental authority, such as the National Institutes of Health. Statistical methods or modeling would be used to relate specific nutrient(s) intake with incidence (or timing) of neurodegenerative disease diagnosis. Other variables, which may include age, sex, education, and/or genetics, would be considered in statistical analysis to understand their effect or interaction with nutrient intakes.

Assessment of neurodegenerative disease pathology: For participants who become deceased during the study and donate their organs, brain autopsies and/or pathologic evaluations of brain specimens would be conducted. Brain specimens would be removed from deceased participants and would be preserved through standard scientific research methods, which may include freezing. Brain specimens could represent a regions of the brain. Neuropathologies, which may include amyloid plaques, neurofibrillary tangles or Lewy bodies, could be identified using microscopy or other imaging methods on sections of brain samples. The level of specific pathologies would be evaluated using quantitative, semi-quantitative or qualitative methods, which could include counts, scores, staging, severity, densities, and/or other necessary measures, standardization or normalization to facilitate analysis. Statistical methods or modeling would be used to relate specific nutrient(s) intake or levels with levels of neurodegenerative disease pathologies. Other variables, which may include age, sex, education, and/or genetics, would be considered in statistical analysis to understand their effect or interaction with nutrient intakes.

For all assessments, stratification may be applied to examine the differential effects of other factors, such as genetic status or physical activity. Also, other measures of brain health or measures related to brain health may be included in such assessments, such as cerebrovascular measures.

Data from the above assessments or related studies may be combined to facilitate composite measures or meta-analyses, which may further indicate the effect of the nutrient combination of interest with brain health-related outcomes.

By evaluating maintenance or improvement in brain health, cognitive decline, incident neurodegenerative disease, and/or neurodegenerative pathologies, the study would provide a cogent indication of whether the nutrient combination of interest exerts protective mechanisms that protect the brain from neurodegenerative disease processes or cognitive changes as people age.

Example 3: Human Real-World Experience

Objective: A human real-world experience study would assess the initial response of study subjects (participants) to the administration of an embodiment, which may include assessments of tolerability, quality of life, and/or exploratory measures of cognitive function.

Methods: Study participants could be healthy adults, adults who exhibit subjective cognitive complaints or adults who may be at-risk of nutrient inadequacies related to brain health. Participants would be naïve to the administration of the embodiment upon enrollment. Participants would follow a prescribed dosing regimen of the embodiment for a pre-defined period of time (for example, 30, 60 or 90 days). The study may be designed to assess change from baseline, change upon cross-over from one regimen to another or difference between parallel groups. For standardization or evaluation purposes, study participants may be asked to complete or maintain a food diary, food frequency questionnaire (FFQ), and/or lifestyle factor survey or diary (for example, including physical activity, social activity or sleep patterns).

Assessments: Prior to the initiation of administration and at pre-defined time points thereafter, each participant would undergo a battery of questions or tests, which could relate to (i) tolerability and adherence, (ii) quality of life, which may include scoring of energy levels, mood, and/or sleep, and/or (iii) cognitive tests, which could characterize cognition across a cognitive domains, such as episodic memory, working memory, semantic memory, visuospatial ability, perceptual speed, and/or other neuropsychological test categories. Responses would be quantitative or semi-quantitative to facilitate analysis. Questionnaires and testing would be conducted either through a clinical site or through a web-enabled or computer platform. Changes in responses across time points and/or across groups or conditions will be assessed.

Cognitive tests could be designed to help inform the design of future experience studies, future prospective observational studies or future clinical studies. Data from the above assessments or related studies may be combined to facilitate composite measures or meta-analyses.

The results of the human real-world experience would confirm the tolerability of an embodiment, as well as provide evidence of its potential to provide a near-term effect on quality of life or cognitive function, as well as provide an indication of its potential to maintain brain health, reduce risk of neurodegenerative disease or reduce risk of cognitive decline.

Example 4: Process of Determining a Dietary Supplement

A basic illustration to help the reader understand how nutrients are assessed is as follows: (i) the MIND diet was evaluated with a community-level cohort and identified as a dietary pattern that is strongly associated with reduced risk of incident neurodegenerative disease and cognitive decline, (ii) one dietary component of the MIND diet is berries, especially those that are darkly pigmented and exhibit a high surface-to-volume ratio, (iii) myricetin, for example, is a polyphenolic compound (a flavonoid) found in rich amounts in berries relative to other dietary components, (iv) epidemiological evidence is emerging that relates myricetin to a number of brain health outcomes, enabling myricetin to pass the primary screen, (v) a dietary inadequacy of myricetin is identified by comparison of USDA dietary guidelines with national- and community-level intakes, and the inadequacy is quantified by use of a composite diet with myricetin-rich foods that meet dietary guidelines (in lieu of a DRI, which has not been established for myricetin), (vi) MOAs of myricetin relevant to neurodegenerative disease hallmarks are confirmed, particularly those involved with oxidative stress and inflammation pathways, and (vii) expected benefit and safety are estimated by assessing epidemiological, clinical, and toxicological data, showing likely benefit with a positive safety profile at the dosages considered to cover dietary intake inadequacy. As a result, myricetin is selected for use in the subject compositions. Other nutrients for the subject compositions are derived using a similar sequence per the method described below.

Figure 2:
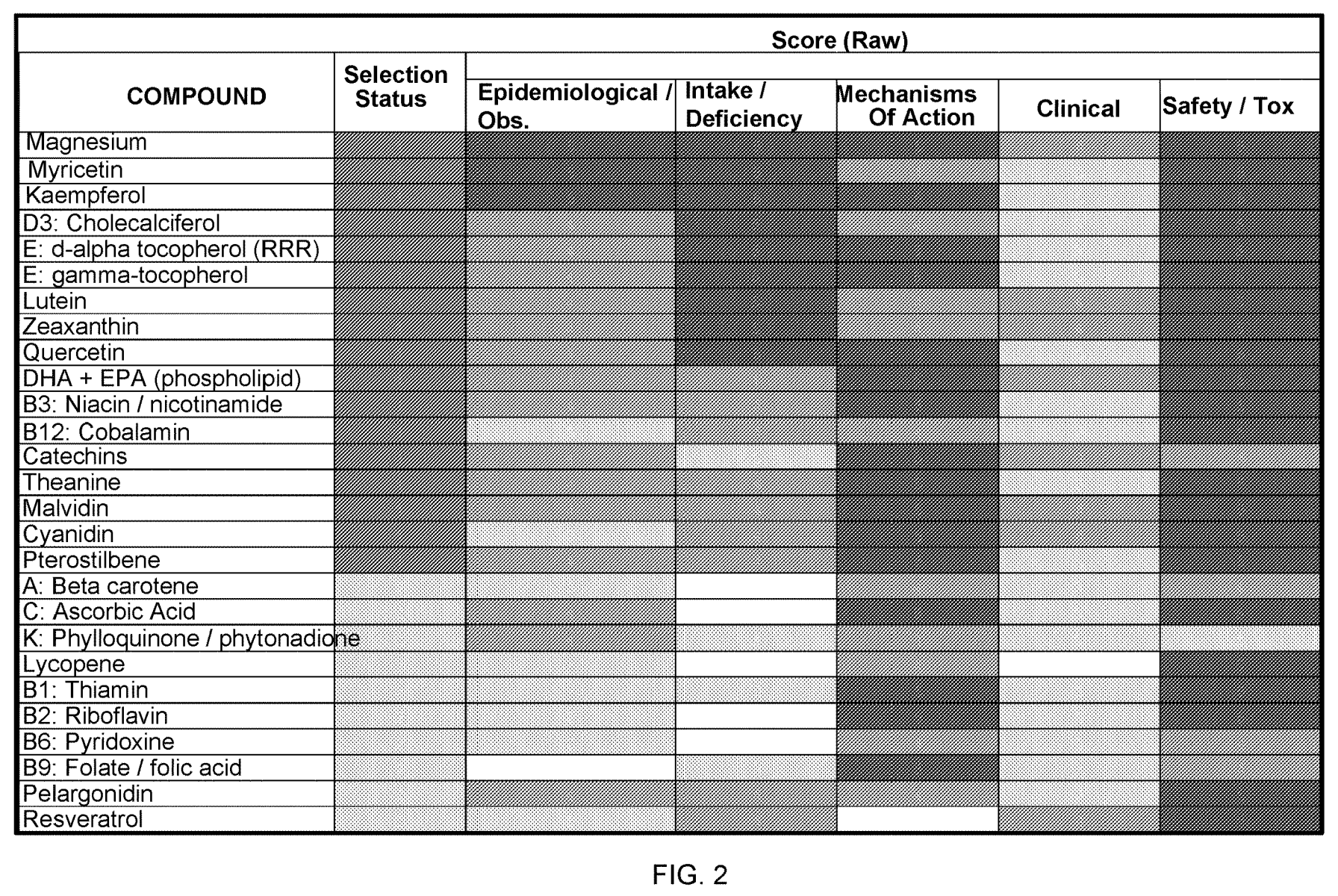

For a selected group of nutrients assessed per this algorithm, an output matrix is shown in FIG. 2.

The process for determining the formulation and specific dosages for a dietary supplement employs a multistage decision-making process to incorporate multiple sources of information. This process (or algorithm) uses a standardized approach that normalizes values and strengths of information sources to provide a single, unified output of candidate nutrients. In contrast to typical formulation of dietary supplements that rely on a single or perhaps two sources of information, this approach allows disparate sources of information to be integrated into a single output.

The inputs for these categories are determined based on quantitative measurements published by the USDA or other research institutions.

Inputs: Food sources categorized by dietary category with similar nutrient profiles.

Input sub layer 1: Individual food sources are separated into distinct inputs based on the micronutrient profiles, and categorization. Each food is categorized as a unique representation of the micronutrient, vitamin, fats as shown in FIG. 1. Mathematically, each food can be represented as the summation of the all the individual nutrients, where each nutrient class has a unique vector of constants K that has been determined for that micronutrient class $$f(\text{unique food}) = \sum_{a}^{i} \begin{pmatrix} K_{a1} \\ K_{a2} \\ \dots \\ K_{an} \end{pmatrix} (a_1 + a_2 \dots) + \begin{pmatrix} K_{b1} \\ K_{b2} \\ \dots \\ K_{bn} \end{pmatrix} (b_1 + b_1 \dots) + \dots$$

Using the above definitions of the food categories or unique foods, we can apply matrix transformations to identify micronutrients that are most representative of a single food or food category. Examples of these transformation would include machine learning methods focused on 1) generative models or cluster analysis such as principal components analysis, hidden markov models or factor analysis or 2) machine learning methods focused on discriminative analysis including linear discriminant analysis, logistic regression, support vector machines or conditional random fields to determine which of the micronutrients are most representative of a single food category and the related reduction in disease states.

Layers 1-4:

For a given food, food category or nutrient, the output of the algorithm is a product of layer 1 and a summation of the following layers. Layers 2 through 4 are weighted calculations to determine the strength of evidence for a particular nutrient. The total evidence weighting for a single nutrient is the summation of layers 2-4, and the multiplication with layer 1 (which is a Boolean operation) either leaves the entire summation unchanged, or sets the dosage to zero.

$$f_{i1\_4}(x) = f_1(x) * \Sigma_{i=2}^{4} f_i(x)$$

Layer 1: This is a Boolean operation which determines whether to proceed with the nutrient analysis. For a given nutrient or micronutrient, analysis only continues if either criteria of having a longitudinal, or cross-sectional human epidemiological study out of which brain health outcomes may be derived. Studies may be scored based on quality of study design or performance, and excluded as a result of this metric. Where the nutrient in question are the $a_1 \ldots b_1 \ldots$ from the previous equation.

$$f_{i1}(\text{nutrient}) = (\text{Longitudinal Epi Study}) \bigvee (\text{Crosssectional Epi Study})$$

Layer 2: A determination of the dietary inadequacy for a given nutrient. This is a weighted calculation that determines the importance of a nutrient, food or food group based on inadequacy within the population or an individual. The total output of layer 2 is determined as follows $$f_{i2}(\text{nutrient}) = K_1 * \left[ 1 - \frac{(e(x, \text{age}) - c(x, \text{age}))}{c(x, \text{age})} \right]$$

where c(x) is an ideal consumption for a given nutrient, micronutrient or food group at a given age.

$$c(x, \text{age}) = \begin{cases} US\ RDI, & \text{if } RDI \text{ exists} \\ f(USDA\ \text{Dietary guidlines}), & \text{if no } RDI \end{cases}$$

where f (USDA Dietary guidlines) is constructed from USDA recommended consumption of foods, or food groups and using those recommended quantities to calculate an exemplary consumption level for specific nutrients or micronutrients.

And where e(x) is the expected consumption for a given nutrient, food or food group as a function of age is derived from epidemiological evidence $$e(x,\text{age}) = f(\text{Epidemiological Evidence})$$

And where $K_1$ is a term that may be used for weighting and is determined based on potential differences in processing or availability of a nutrient. This may be used to provide personalization for a specific individual given additional information such as genotype, family history, lifestyle factors, etc $$K_1 = f(\text{genotype,microbiome,etc})$$

Layer 3: A determination of the evidentiary strength for a given nutrient given the known mechanisms of action (MOA) for a given nutrient, and importance of the MOA to specific known hallmarks of neurodegenerative disease. This is a weighted calculation that determines the importance of a single nutrient to this layer.

$$f_{i3}(\text{nutrient}) = f_{H1}(\text{nutrient}) + f_{H2}(\text{nutrient}) \ldots + f_{Hn}(\text{nutrient})$$

where $f_H$ are biochemical and physiological hallmarks of neurodegeneration. Examples are oxidative stress, metabolic dysfunction or $$f_{H1} = K_{H1} * \Sigma_{i=1}{}^n P(\text{Harm Reduction|Nutrient MOA}_i)$$

Where $K_{H1}$ is weighting constant that incorporates the strength and importance of the hallmark to the progression of the disease, thus $K_{H1} = f$ (Hallmark Importance). This may be used to provide personalization for a specific individual given additional information such as genotype, family history, lifestyle factors, etc. For example, an individual who works with pesticides and has a family history of Parkinson's may have an increased weighting for toxin clearance compared with an office worker.

$$K_{H1} = f(\text{Hallmark Importance|genotype,microbiome, etc})$$

And where P (Harm Reduction|Nutrient MOA$_i$) is an output given the number, quality and type of experiments used to determine the nutrient MOA. This would be determined based on the appropriateness for a disease state. For example, nutrient MOAs that have been studied using multiple animal model would increase confidence more than a single study performed using cell culture.

Layer 4: A determination of the evidentiary strength for a given nutrient or food given human clinical evidence (random controlled trials—RCT) and human epidemiological data. Layer 1 incorporated epidemiological data, but this was used exclusively to generate a binary output, whereas this is a weighted calculation that averages the clinical and epidemiological evidence.

$$f_{i4}(\text{nutrient}) = \frac{f_{CE}(\text{nutrient}) + f_{EPI}(\text{nutrient})}{2}$$

Where $$f_{CE}(\text{nutrient}) = \frac{\sum_i^m K_{CE\_i} * \frac{Dosage_i}{c(\text{nutrient})}}{\sum_i^m K_{CE\_i}}$$

Where $K_{CE\_i}$ is a weighting constant that incorporates that quality of the experimental design, and the reported outcome. Dosages used in clinical experiments both with higher quality, and better outcomes receive higher weights. And where c(nutrient) is the ideal consumption for a given nutrient, micronutrient or food group at a given age as given in the description of layer 2.

Where $$f_{EPI}(\text{nutrient}) = \frac{\sum_i^m K_{EPI\_i} * \frac{TC_i}{c(\text{nutrient})}}{\sum_i^m K_{EP\_i}}$$

Where $K_{EPI\_i}$ is a weighting constant that incorporates that quality of the experimental design, and the reported outcome. Epidemiological experiments both with higher quality design and data, and better outcomes receive higher weights. Where $TC_i$ is the mean consumption for the given nutrient in the highest group studied (quartile, quintile, etc). And where c(nutrient) is the ideal consumption for a given nutrient, micronutrient or food group at a given age as given in the description of layer 2.

Layer 5: This is a safety and tolerability limit imposed on the dosage level. This incorporates information about safety and toxicity clinical studies, as well as the upper limit suggested by the DRI (if available). Critically, the weightings at layers 2-4 are designed so that the final output is within the range of 0-5. And this weighting is then used to determine final recommended dosage.

$$r(\text{nutrient}) = f_{safety}(f_{i1-4}(\text{nutrient}) * c(\text{nutrient}), \text{nutrient})$$

Where the recommended dosage for a single nutrient is the weighted output of layers 1-4 as detailed above, multiplied by c(x) which the ideal consumption for a given nutrient, micronutrient or food group at a given age as given in the description of layer 2.

The safety function determines the upper limit of dosage and ensures that the recommended dosage falls below that. This is calculated by taking the minimum of desired dosage, and two upper limits.

$$f_{safety}(x,\text{nutrient})=\min(x,K_{DRI}*UL_{RDI}(\text{nutrient}), K_{TOX}*UL_{TOX}(\text{nutrient}))$$

where $UL_{DRI}$ is determined using the DRI upper limit if it exists for the specific nutrient and where the domain of the safety factor $K_{DRI}$ is [0, 1). Similarly, $UL_{TOX}$ is determined as an upper limit from clinical toxicological and tolerability research and where the domain of the safety factor $K_{TOX}$ is [0, 1).

The invention claimed is:

1. A dietary supplement comprising: a water-soluble vitamin component containing about 25 mg-to about 75 mg vitamin B3 and about 0.0-1 mg to about 0.10 cyanocobalamin, an oil-soluble vitamin component containing about 0.021 mg to about 0.04 mg vitamin D and about 4910 mg to about 80mg vitamin E, magnesium or derivative thereof at about 25 mg to about 75 mg, a primary polyphenolic compound containing about 5 mg to about 15 mg myricetin or derivative thereof, about 10 mg to about 30 mg kaempferol or derivative thereof, and about 25 mg-to about 75 mg quercetin or derivative thereof, a secondary polyphenolic compound containing about 5 mg to about 400 mg of malvidin or derivative thereof, about 7.5 mg-to about 500 mg of cyanidin or derivative thereof, about 1 mg to about 12mg lutein or derivative thereof, about 0.0125 mg to about 0.0500 mg pterostilbene or derivative thereof, and about 80 mg to about 375 mg of a catechin composition, and an omega-3-phospholipid complex containing about 50 mg to about 300 mg of docosahexaenoic acid (DHA) and about 15 mg to about 70 mg of eicosapentaenoic acid (EPA), wherein the supplement is formulated into one or more dosage forms.

2. The dietary supplement of claim 1, wherein the vitamin B3 is nicotinamide in an amount of about 50 mg.

3. The dietary supplement of claim 1, wherein the vitamin B12 is cyanocobalamin in an amount of about 0.020 mg.

4. The dietary supplement of claim 1, wherein the vitamin D is cholecalciferol in an amount of about 0.030 mg.

5. The dietary supplement of claim 1, wherein the vitamin E is in the form of d-alpha-tocopherol in an amount of about 20 mgand gamma-tocopherol in an amount of about 40 mg.

6. The dietary supplement of claim 5, wherein the ratio of gamma-tocopherol: d-alpha-tocopherol is about 2:1.

7. The dietary supplement of claim 1, wherein the magnesium derivative is magnesium bisglycinate chelate, and wherein the magnesium component is in an amount of about 50 mg.

8. The dietary supplement of claim 1, wherein the ratio of kaempferol or derivative thereof: myricetin or derivative thereof is about 2:1.

9. The dietary supplement of claim 1, wherein the kaempferol or derivative thereof and myricetin or derivative thereof are at a purity greater than 90%.

10. The dietary supplement of claim 1, wherein the myricetin is in an amount of about 10 mg, the kaempferol is in an amount of about 20 mg, and the quercetin is in an amount of about 50 mg.

11. The dietary supplement of claim 1, wherein the malvidin is in an amount of about 10 mgand the cyanidin is in an amount of about 15 mg.

12. The dietary supplement of claim 1, wherein the lutein or derivative thereof is a combination of lutein and zeaxanthin in an amount of about 6 mg.

13. The dietary supplement of claim 1, wherein the pterostilbene is in an amount of about 0.025 mg.

14. The dietary supplement of claim 1, wherein the catechin composition contains catechins in an amount of about 160 mgand l-theanine in an amount of about 50 mg.

15. The dietary supplement of claim 1, wherein the DHA is in a phospholipid form and wherein the DHA is in an amount of about 200 mg, and the EPA is in a phospholipid form and wherein the EPA is in an amount of about 58 mg.

16. The dietary supplement of claim 1, wherein the dietary supplement is formulated into dosage form 1 and dosage form 2.

17. The dietary supplement of claim 16, wherein dosage form 1 comprises: about 25 mg nicotinamide, about 0.010 mg cyanocobalamin, about 25 mg magnesium, about 25 mg quercetin, about 5 mg myricetin, about 10 mg kaempferol, about 5 mg of malvidin, about 7.5 mg of cyanidin, about 0.0125 mg pterostilbene, and about 105 mg of a combination of catechins and 1-theanine.

18. The dietary supplement of claim 16, wherein dosage form 2 comprises:

about 0.030 mg cholecalciferol, about 20 mg d-alpha-tocopherol, about 40 mg gamma-tocopherol, about 6 mg of a combination of lutein and zeaxanthin, about 200 mg phospholipid/phosphatidylcholine docosahexaenoic acid (DHA), and about 58 mg phospholipid/phosphatidylcholine eicosapentaenoic acid (EPA).

* * * * *